United States Patent
Giannini et al.

(10) Patent No.: US 8,927,533 B2
(45) Date of Patent: Jan. 6, 2015

(54) THIO DERIVATIVES BEARING LACTAMS AS POTENT HDAC INHIBITORS AND THEIR USES AS MEDICAMENTS

(71) Applicant: SIGMA-TAU Industrie Farmaceutiche Riunite S.p.A., Rome (IT)

(72) Inventors: Giuseppe Giannini, Pomezia (RM) (IT); Walter Cabri, Rozzano (MI) (IT); Gianfranco Battistuzzi, Rome (IT); Davide Vignola, Aprilia (LT) (IT); Nicola Fanto', Pomezia (RM) (IT); Claudio Pisano, Aprilia (LT) (IT); Loredana Vesci, Rome (IT)

(73) Assignee: SIGMA-TAU Industrie Farmaceutiche Riunite S.p.A., Rome (IT)

(*) Notice: Subject to any disclaimer, the term of this patent is extended or adjusted under 35 U.S.C. 154(b) by 0 days.

(21) Appl. No.: 14/236,359

(22) PCT Filed: Sep. 17, 2012

(86) PCT No.: PCT/EP2012/068230
§ 371 (c)(1),
(2) Date: Jan. 31, 2014

(87) PCT Pub. No.: WO2013/041480
PCT Pub. Date: Mar. 28, 2013

(65) Prior Publication Data
US 2014/0200205 A1     Jul. 17, 2014

(30) Foreign Application Priority Data
Sep. 19, 2011 (EP) .................... 11181832

(51) Int. Cl.
| | | |
|---|---|---|
| A61K 31/397 | (2006.01) | |
| A61K 31/4412 | (2006.01) | |
| C07D 205/08 | (2006.01) | |
| C07D 211/40 | (2006.01) | |
| C07D 207/24 | (2006.01) | |
| C07D 213/69 | (2006.01) | |
| C07D 401/04 | (2006.01) | |
| C07D 207/277 | (2006.01) | |
| C07D 207/28 | (2006.01) | |
| C07D 211/78 | (2006.01) | |
| C07D 207/46 | (2006.01) | |
| C07D 211/94 | (2006.01) | |
| C07D 401/12 | (2006.01) | |

(52) U.S. Cl.
CPC ............ *C07D 213/69* (2013.01); *C07D 401/04* (2013.01); *C07D 205/08* (2013.01); *C07D 207/277* (2013.01); *C07D 207/28* (2013.01); *C07D 211/78* (2013.01); *C07D 207/46* (2013.01); *C07D 211/94* (2013.01); *C07D 401/12* (2013.01)
USPC ...... 514/210.02; 514/327; 514/423; 540/200; 546/221; 548/537

(58) Field of Classification Search
None
See application file for complete search history.

(56) References Cited

U.S. PATENT DOCUMENTS
6,511,990 B1    1/2003  Breslow et al.

OTHER PUBLICATIONS

Chuang, De-Maw. Trends in Neurosciences. 32(11). (2009) 591-601.*
MedlinePlus. Degenerative Nerve Diseases. (2014) <http://www.nlm.nih.gov/medlineplus/degenerativenervediseases.html>.*
MedicineNet.com. <http://www.medterms.com>, 2004.*
Vojinovic, Jelena. Mol Med 17:5-6 (2011) 397-403.*
Andrews, KT. Curr. Top Med. Chem. 9:3 (2009) 292-308.*

* cited by examiner

*Primary Examiner* — Golam M M Shameem
*Assistant Examiner* — Laura Daniel
(74) *Attorney, Agent, or Firm* — Lucas & Mercanti, LLP

(57) ABSTRACT

The present invention relates to novel amide compounds of Formula (I), and their use as anti-tumoral and pro-apoptotic agents. The invention includes the use of such compounds in medicine, in relation to cancer disease as well as other diseases where an inhibition of HDAC is responsive, and the pharmaceutical composition containing such compounds.

11 Claims, 1 Drawing Sheet

Formula I

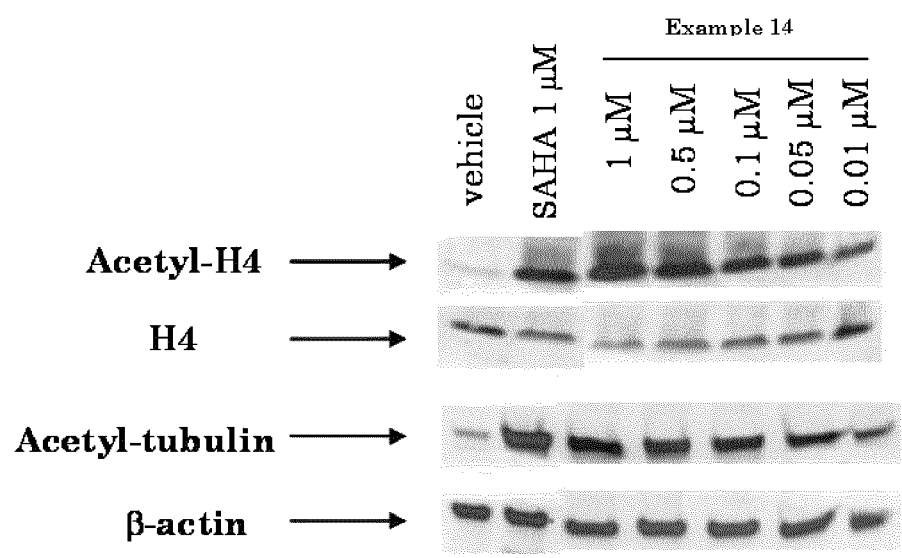

THIO DERIVATIVES BEARING LACTAMS AS POTENT HDAC INHIBITORS AND THEIR USES AS MEDICAMENTS

This application is a U.S. national stage of PCT/EP2012/068230, filed Sep. 17, 2012, which claims priority to and the benefit of European Application No. 11181832.4, filed Sep. 19, 2011, the contents of each of which are incorporated herein by reference.

FIELD OF THE INVENTION

The present invention relates to novel thio compounds and their use as medicaments. The invention includes the use of such compounds and of the pharmaceutical composition containing such compounds in medicine, in relation to cancer diseases, inflammatory diseases, neuronal diseases, parasite infections (e.g., Plasmodium infection), as well as other diseases where an inhibition of HDAC is responsive.

BACKGROUND OF THE INVENTION

Histone deacetylases (HDACs) are a family of enzymes found in numerous organisms among which bacteria, fungi, plants, and animals. Such enzymes catalyze the removal of acetyl groups from ε-N-acetylated lysine residues of various protein substrates including histones, transcription factors, α-tubulin, and nuclear importers. Up to date eighteen HDAC isoforms have been characterized. They are classified in four different families with regard to their DNA sequence similarity and their biological role within the cells.

HDAC1, HDAC2, HDAC8 and HDAC3 are members of class-I. The first three isoforms are primarily found in the nucleus; meanwhile HDAC3 is also found in the cytoplasm or membrane-associated.

HDAC4, HDAC5, HDAC6, HDAC7, HDAC9 and HDAC10 form class-II. This class has been further divided in two sub-classes, class IIa (HDAC4, 5, 7 and 9) and class IIb (HDAC6 and 10). Class-II enzymes are expressed in a limited number of cell types and either shuttle between the nucleus and cytoplasm (i.e., class-IIa), or are mainly cytoplasmic (i.e., class-IIb) (Yang X. J., et al., Mol. Cell. Biol., 2005, 25, 2873).

Class-IV comprises only one member (HDAC11), meanwhile class-III, also called sirtuins, is composed of NAD+ dependent enzymes. The common feature of classes I, II and IV enzymes resides in their zinc dependent nature. HDAC inhibitors (HDACi) have been shown to be potent inducers of growth arrest, differentiation and apoptotic cell death of transformed cells in vitro and in vivo.

HDAC inhibition was also shown to lead to the reduction of inflammation in models of autoimmune and inflammatory diseases (Leoni F., et al., Proc. Natl. Acad. Sci., 2002, 99, 2995).

One of the first compounds to have been documented as HDACi was the well-known anti-epileptic valproic acid, which inhibits all isoforms of classes I, II and IV. Once recognized the important role of this family of enzymes in the development of cancer, many efforts directed to find potent HDACi were undertaken by numerous academic groups as well as by pharmaceutical companies.

Vorinostat, originally known as SAHA (suberoylanilide hydroxamic acid), was the first-in-class small molecule hydroxamate derivative HDACi to have been approved by the FDA in 2006 to treat a rare cancer, cutaneous T-cell lymphoma in patients who have received at least one prior systemic therapy (Grant S., et al., Nature Rev. Drug Discov., 2007, 6, 21). SAHA is a potent HDACi inhibiting classes I and II as the vast majority of HDACi currently in clinical trials (Paris M., et al., J. Med. Chem., 2008, 51, 1505).

Actually, according to their structures, the various families of inhibitors can be grouped, in four main groups:
a) short chain fatty acids (e.g., sodium butyrate, phenylbutyrate, pivanex (pivaloyloxymethyl butyrate, AN-9), and valproic acid);
b) hydroxamates (e.g., SAHA, belinostat (PXD101), panobinostat (LBH589), dacinostat (LAQ-824), and trichostatin);
c) cyclic derivatives (e.g., romidepsin or FK-228);
d) benzamide (e.g., entinostat (MS-275), mocetinostat (MGCD-0103) and acetyldinaline (CI-994)).

Some clinical trials involving combination therapies have been conducted, to assess the efficacy of broad spectrum HDACi in combination with standard chemotherapeutic agents, (e.g., docetaxel and vorinostat), in patients with advanced and relapsed lung, bladder, or prostate cancer (clinical trial NCT00565227). HDAC has been hypothesized as a potential target for the treatment of parasite infections (e.g., Plasmodium infection) about thirteen years ago. If most efforts from the scientific community have been dedicated to the identification of selective HDACi, there is still a large medical need for pan inhibitors since it has been demonstrated that the various cancer diseases do not involve the same HDAC isoforms. Moreover, the scientific community is also divided with regard the assessment of specific HDAC isoforms to specific cancers (Giannini G., et al., Future Medicinal Chemistry, 2012, 4, 11, 1439-1460). Indeed, HDAC1 is up-regulated in prostate cancer (Halkidou K., et al., Prostate, 2004, 59, 177) and gastric cancer (Choi J. H., et al., Jpn. J. Cancer Res., 2001, 92, 1300), HDAC2 is up-regulated in gastric cancer (Song J., et al., APMIS, 2005, 113, 264), HDAC3 is up-regulated in lung cancer (Bartling B., et al., Lung Cancer, 2005, 49, 145) and there is elevated expression of HDAC6 in oral squamous cell carcinoma (Sakuma T., et al., J. Oncol., 2006, 29, 117).

The involvement of HDAC in further diseases such as neurodegenerative diseases (Chuang D. M., et al., Trends in Neuroscience, 2009, 32, 11, 591; Sleiman S. F., et al., Expert Opin. Investig. Drugs, 2009, 18, 5, 573), cardiac hypertrophy (Hamamori Y., et al., J. Clin. Invest., 2003, 112, 6, 824) has also been documented. A recent review details diseases for which HDAC inhibition is recognized as a new approach (Dinarello C. A., et al., Mol. Med., 2011, 17, 333).

The bidendate hydroxamic acid moiety is recognized to be one of the best zinc binding-group, and a multitude of HDAC inhibitors bearing such moiety has been developed (Sampath-Kumar A., et al., Bioorg. Med. Chem. Lett., 2005, 15, 8, 1969). However, such functionality has also been associated with poor pharmacokinetic properties (Colletti S., et al., Bioorg. Med. Chem. Lett., 2001, 11, 107) as well as with sustained toxicity (Suzuki T., Cur. Med. Chem., 2005, 12, 24, 2867). Therefore, a lot of efforts has been devoted to the identification of new HDACi that could demonstrate high binding affinity toward the biological target as well as potent cellular activity. A review published lately (Bertrand P., Eur. J. Med. Chem., 2010, 45, 2095), assessed the binding affinity and biological properties of various non-hydroxamate based derivatives, among which thio adducts were disclosed, hypothesizing that the latter could potentially have an orientation within the active site of the protein completely different from the one of hydroxamate analogues.

If HDACi containing a straight thio-binding group have been studied no such derivatives have however entered clinical trial so far.

Bertrand P. also proposed that FK228 biological activity was due to the reduction of the disulfide bond to lead to the thio adduct 1, the latter being the active entity as depicted in scheme 1 underneath.

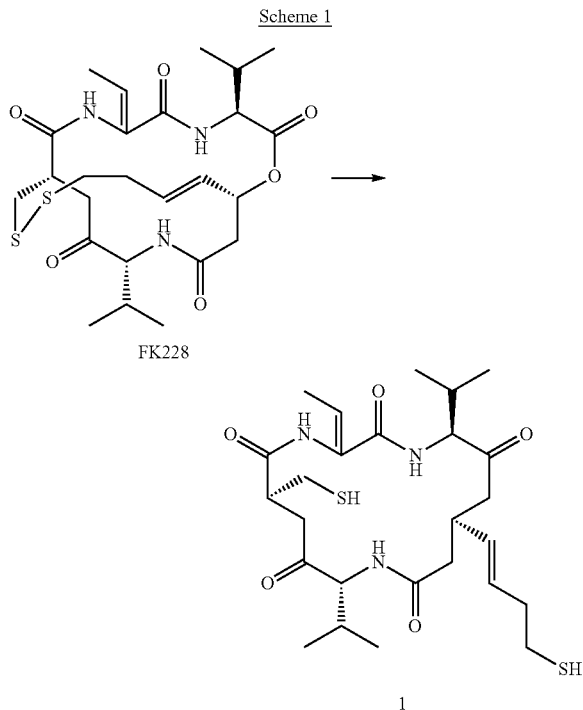

However, this mechanism of action of FK228 can be questioned in front of U.S. Ser. No. 12/845,658 which hypothesized another metabolite to be the active species. Unfortunately, since no biological activity of the various theorized metabolites was shown, no clear teaching could be gathered from this work.

The straight thio analogue of SAHA (scheme 2) has been synthesized (Suzuki T., et al., *Bioorg. Med. Chem. Lett.*, 2004, 14, 3313) and both compounds demonstrated similar HDAC affinity.

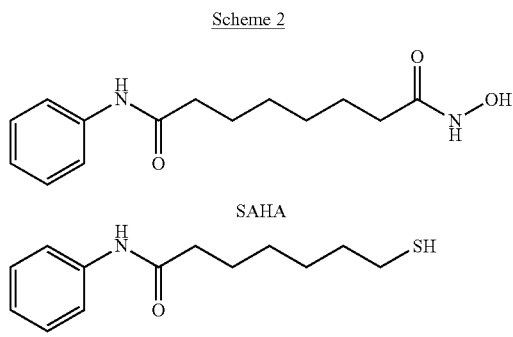

Suzuki T., et al. further disclosed more potent thio-containing metal binding groups (MBG) HDACi bearing a sterically more hindered amide moiety such as biphenyl, benzofuran, indole or quinoline instead of the phenyl group of SAHA (Suzuki T., et al., *J. Med. Chem.*, 2005, 48, 1019).

JP2007238452 disclosed derivatives of Formula 2, wherein the carbon atom in position α with respect of the carbonyl amide was substituted by a carbamate moiety (i.e., $R^2=CO_2R$).

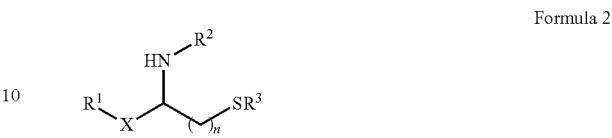

Formula 2

Such derivatives have also been disclosed later reporting optimization of the CAP group (Suzuki T., et al., *J. Med. Chem.*, 2006, 49, 4809) and/or the spacer (Itoh Y., et al., *J. Med. Chem.*, 2007, 50, 5425). Interestingly, such derivatives were disclosed as HDAC6 selective. In particular, Itoh Y. disclosed derivatives bearing medium-sized amino substituents in position α with respect of the carbonyl amide which have been found to be HDAC6 selective supposedly because of the absence of hydrophobic pocket to accept such groups in the other isoforms.

It is also generally recognized that thio derivatives are one Log unit less active than their hydroxamate counterpart (Wang D., et al., *J. Org. Chem.*, 2007, 72, 5446). SAHA has shown beneficial effects in a model of focal cerebral ischemia (Faraco G., et al., *Mol. Pharmacol.*, 2006, 70, 6, 1876).

Therefore, a great need still exists in providing new HDAC inhibitors presenting low-nanomolar binding affinity toward the HDAC proteins as well as potent cellular activity.

DESCRIPTION OF THE INVENTION

It has now been found that new thio derivatives are endowed with potent inhibitory activity against HDAC.

The invention provides compounds of Formula (I) or a salt, hydrate or solvate thereof, in the preparation of a composition for inhibition of HDAC activity:

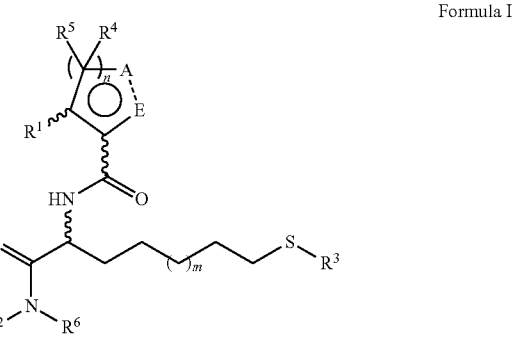

Formula I wherein,
$R^1$ is H, $(C_1-C_6)$-alkyl or aryl; or alternatively
$R^1$ and one $R^4$, each being linked to two adjacent carbon atoms, in case n is 2 or 3, are taken together to form a cyclopropane ring;
$R^2$ is phenyl optionally substituted with halogen, benzyloxy, $(C_1-C_3)$-alkyl or $CF_3$; $(C_3-C_6)$-cycloalkyl; aryl-$(C_1-C_6)$-alkyl wherein the aryl is optionally substituted with benzyloxy, $(C_1-C_3)$-alkyl or $CF_3$;
$R^3$ is H, $PO(OH)_2$, or a group of Formula (II)

—(CO)—$R^7$    Formula II $R^7$ is $(C_1-C_7)$-alkyl, $(C_1-C_6)$-alkoxy or —CH(NH$_2$)R$^8$;

$R^8$ is H, or the side chain of a natural α-amino acid;

$R^4$ and $R^5$ are at any occurrence independently H, halogen, $(C_1-C_6)$-alkyl, or alternatively, when n is 2 or 3, one $R^4$ and one $R^5$, each being linked to two adjacent carbon atoms, are taken together to form a cyclopropane ring;

$R^6$ is H or alternatively, $R^2$ and $R^6$ are taken together to form a five- to six-membered heterocycle which can be optionally fused with an aryl moiety;

-A-E- is —(CO)—(NR$^9$)— or —(NR$^9$)—(CO)—;

$R^9$ is H or $(C_1-C_3)$-alkyl;

m is an integer comprised between 0 to 3;

n is an integer comprised between 0 to 3 with the proviso that when is 2 or 3, each of $R^4$ and $R^5$ can adopt different meaning at each occurrence;

the symbol ⌇ means that the carbon atom bearing said symbol can adopt a R or S configuration;

the symbol ○ can be absent, but if present it means that the cycle can be partially unsaturated with the proviso that when the carbon atom bearing $R^4$ is involved in a double bond, $R^5$ is absent;

their tautomers, their geometrical isomers, their optically active forms such as enantiomers, diastereomers and their racemate forms, as well as their pharmaceutically acceptable salts thereof.

An embodiment of this invention is that of compounds of Formula (I), for use as medicaments.

In a further embodiment, said medicament is used for treating a subject affected by cancer diseases, inflammatory diseases, neuronal diseases and parasite infections (e.g., Plasmodium infection).

The invention furthermore provides a process for the preparation of compounds of Formula (I), involving conventional synthetic methods which are described underneath.

Compounds of general Formula (I) can be obtained by reacting compounds of Formula (III),

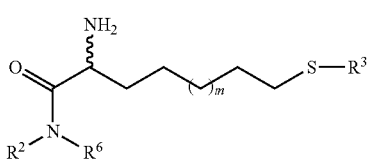

Formula III wherein $R^2$, $R^3$ and $R^6$ and m are as above described, with compounds of Formula (IV) or of an organic salt of them,

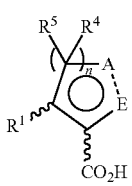

Formula IV wherein $R^1$, $R^4$ and $R^5$, -A-E- and n are as above described, in a polar aprotic solvent in the presence of a coupling agent well-known to those skilled in the art of peptidic coupling.

Compounds of general Formula (I), wherein $R^3$ is H, can be obtained by reacting compounds of Formula (I) wherein $R^3$ is a group of Formula (II) as above defined, all other substituents and parameters being as above defined, with sodium hydroxide in a polar solvent. Alternatively, such compounds can be obtained by replacing in the above-mentioned reaction sodium hydroxide by sodium thiomethoxide using a described procedure (Wallace O. B., et al., *Tetrahedron Letters,* 1998, 39, 2693). Compounds of general Formula (III) can be obtained by reacting compounds of Formula (V),

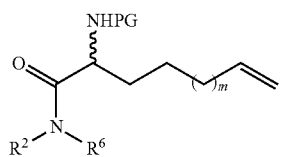

Formula V wherein $R^2$ and $R^6$ and m are as above described, and wherein PG refers to an amino protecting group, such as for example, t-butoxycarbonyl, with compounds of Formula (VI), R$^3$SH      Formula VI wherein $R^3$ is as above described, in the presence of a radical initiator such as AIBN in a polar solvent at a temperature up to 80° C.

In all said transformations, any interfering reactive group can be protected and then deprotected according to well-established procedures described in organic chemistry (e.g., Greene T. W. and P. G. M. Wuts "Protective Groups in Organic Synthesis", J. Wiley & Sons, Inc., 3rd Ed., 1999) and well-known to those skilled in the art. All said transformations are only examples of well-established procedures described in organic chemistry (e.g., March J., "Advanced Organic Chemistry", J. Wiley & Sons, Inc., 4th Ed., 1992) and well-known to those skilled in the art.

The terms "$(C_1-C_x)$-alkyl", "$(C_1-C_x)$-alkoxy", and "$(C_3-C_x)$-cycloalkyl", wherein x is an integer comprised between 2 and 7 (integer comprised between 4 and 7 with regard to the cycloalkyl), alone or encompassed in a more complex structure, refer to linear or branched alkyl, linear or branched alkoxy having from 1 to 7 carbon atoms or cycloalkyl groups having from 3 to 7 carbon atoms.

The terms "heterocycloalkyl" and "heterocycle" refer to a saturated or partially unsaturated (but not aromatic) four-, five-, six- or seven-membered ring containing at least one nitrogen atom and optionally one or more further heteroatoms which may be the same or different selected from the group consisting of nitrogen, oxygen and sulfur, and which rings may be substituted with amino or alkyl moieties. Preferred heterocycloalkyl include azetidine, pyrrolidine, piperidine, piperazine, ketopiperazine, 2,5-diketopiperazine, morpholine and thiomorpholine. Six-membered heterocycloalkyl can be optionally fused with an aryl as defined underneath. Preferred such fused heterocycles are for example tetrahydroquinoline and tetrahydroisoquinoline.

The term "aryl" refers to an aromatic carbocyclic group of 6 to 14 carbon atoms having a single ring (e. g., phenyl) or multiple rings that may be attached in a pendent manner or may be fused. Preferred aryl include phenyl, naphthyl, phenantrenyl, biphenyl and the like. Said "aryl" may have 1 to 3 substituents chosen among hydroxyl, halogen, haloalkyl, cyano, $(C_1-C_x)$-alkyl, $(C_1-C_x)$-alkoxy, benzyloxy, amino, aminoalkyl or alkylamino.

The term "amino" refers to the group —NH$_2$.

The term "alkylamino" refers to the group —NHR where R is "$(C_1-C_x)$-alkyl" as defined above.

The term "aminoalkyl" refers to the $(C_1-C_x)$-alkyl as defined above which is substituted by an amino group.

The term "haloalkyl" refers to $CF_3$ or $CHF_2$ moieties or to alkyl groups as previously defined containing $CF_3$ or $CHF_2$ moieties.

The term "aryl-$(C_1-C_6)$-alkyl" refers to alkyl groups as defined above, having one aryl substituent as defined above. Preferred aryl-$(C_1-C_6)$-alkyl include benzyl, phenethyl, diphenyl methyl and the like.

The expression "natural α-amino acid" refers to the 20 natural amino acids, in all possible isomeric forms and consisting of glycine, alanine, phenylalanine, valine, leucine, isoleucine, aspartic acid, asparagine, glutamic acid, glutamine, serine, lysine, histidine, methionine, proline, cysteine, threonine, tryptophan, arginine and tyrosine.

The term cancer means malignant neoplasm which invades and destroys the surrounding tissue and may form metastases and eventually can kill the host. "Pharmaceutically acceptable salts" refers to salts of the below identified compounds of Formula (I), that retain the desired biological activity. Examples of such salts include, but are not restricted to acid addition salts formed with inorganic acids (e. g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, toluene sulfonic acid, naphthalene disulfonic acid, methanesulfonic acid, and poly-galacturonic acid.

We have found that the derivatives (I) and their pharmaceutically acceptable salts, prepared according to the invention, are useful agents for the treatment of disease states, disorders and pathological conditions mediated by HDAC; in particular for the treatment of cancer diseases, inflammatory diseases, neuronal diseases and parasite infections (e.g., Plasmodium infection).

The pharmaceutical compositions will contain at least one compound of Formula (I) as an active ingredient, in an amount such as to produce a significant therapeutic effect. The compositions covered by the present invention are entirely conventional and are obtained with methods which are common practice in the pharmaceutical industry, such as, those illustrated in Remington's Pharmaceutical Science Handbook, Mack Pub. N.Y.—last edition. According to the administration route chosen, the compositions will be in solid or liquid form, suitable for oral, parenteral or topical administration. The compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

Generally, the compounds of this invention are administered in a "therapeutically effective amount". The amount of the compound actually administered will typically be determined by a physician, in the light of the relevant circumstances, including the condition to be treated, the chosen route of administration, the actual compound administered, drug combination, age, body weight, response of the individual patient, the severity of the patient's symptoms, and the like. For any compound, the therapeutically effective dose can be estimated initially either in cell culture assays or in animal models, usually mice, rats, guinea pigs, rabbits, dogs, or pigs. Animal models may also be used to determine the appropriate concentration range and route of administration. Such information can then be used to determine useful doses and routes for administration in humans. In calculating the Human Equivalent Dose (HED) it is recommended to use the conversion table provided in Guidance for Industry and Reviewers document (2002, U.S. Food and Drug Administration, Rockville, Md., USA).

Generally, an effective dose will be from 0.01 mg/kg to 100 mg/kg, preferably 0.05 mg/kg to 50 mg/kg. For any compound, the therapeutically effective dose can be estimated initially either in cell culture assays or in animal models, usually mice, rats, guinea pigs, rabbits, dogs, or pigs. The precise effective dose for a human subject will depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician.

Compositions may be administered individually to a patient or may be administered in combination with other agents, drugs or hormones.

The medicament may also contain a pharmaceutically acceptable carrier, for administration of the therapeutic agent. Such carriers include antibodies and other polypeptides, genes and other therapeutic agents such as liposomes, provided that the carrier does not induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol.

Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The medicament of this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means.

The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include refilled, premeasured ampoules or syringes of the liquid compositions or pills, tablets, capsules or the like in the case of solid compositions. In such compositions, the compound of the invention is usually a minor component (from about 0.1 to about 50% by weight or preferably from about 1 to about 40% by weight) with the remainder being various vehicles or carriers and processing aids helpful for forming the desired dosing form. Dosage treatment may be a single dose schedule or a multiple dose schedule. As above disclosed, the compounds of the present invention are useful as medicaments due to their HDAC inhibiting properties for the treatment of disorders where such inhibition result in improving the health of the patient. In particular, patients suffering from cancer and inflammatory diseases.

The compositions in question may, together with the compounds of Formula (I), contain further known active principles.

A further object of the invention is a process for the preparation of pharmaceutical compositions characterised by mixing one or more compounds of Formula (I) with suitable excipients, stabilizers and/or pharmaceutically acceptable diluents.

An embodiment of this invention is that of compounds of Formula (I) described earlier, wherein n is 1 or 2.

A preferred embodiment of this invention is that of compounds of Formula (I) described earlier, wherein $R^3$ is a group of Formula (II) as described above.

According to another embodiment of the present invention the cancer to be treated is a primary tumour, selected from the group comprising sarcoma, carcinoma, melanoma, bone tumour, neuroendocrine tumour, lymphoid leukaemia, myeloid leukaemia, monocytic leukaemia, megakaryocytic leukaemia, acute promyelocytic leukaemia or Hodgkin's disease.

The above mentioned sarcoma and carcinoma consist of the group comprising: breast cancer; lung cancer, including non-small cell lung cancer (NSCLC) and small-cell lung cancer (SCLC); gastrointestinal cancer, including oesophageal, gastric, small bowel, large bowel, rectal and colon cancer; glioma, including glioblastoma; ovarian cancer; cervical cancer; endometrial cancer; mesothelioma; renal cancer; prostate cancer; peritoneum cancer; pleura cancer; face and neck cancer; bladder cancer; brain cancer; and cancer of the skin or the eyes.

The neoplasm can also refer to a pediatric cancer. For example pediatric cancers that can be treated or where the progression of the condition can be delayed according to the present invention are selected from the group consisting of: acute lymphoblastic leukaemia, acute myeloid leukaemia, adrenocortical carcinoma, astrocytomas, bladder cancer, brain stem glioma, central nervous system atypical teratoid/rhabdoid cancer, brain cancer, central nervous system embryonal cancers, brain cancer, astrocytomas, craniopharyngioma, ependymoblastoma, ependymoma, childhood medulloblastoma, medulloepithelioma, pineal parenchymal cancers of intermediate differentiation, supratentorial primitive neuroectodermal cancers and pineoblastoma, breast cancer, bronchial cancers, carcinoid cancer, cervical cancer, chordoma, colorectal cancer, oesophageal cancer, extra cranial germ cell cancer, gastric cancer, glioma, hepatocellular (liver) cancer, Hodgkin lymphoma, kidney cancer, laryngeal cancer, leukaemia, acute lymphoblastic/myeloid leukaemia, liver cancer, non-Hodgkin lymphoma, medulloblastoma, mesothelioma, multiple endocrine neoplasia syndrome, nasopharyngeal cancer, oral cancer, ovarian cancer, pancreatic cancer, papillomatosis, renal cell cancer, rhabdomyosarcoma, salivary gland cancer, sarcoma, skin cancer, thymoma and thymic carcinoma, thyroid cancer and vaginal cancer.

Still another embodiment of the present invention consists of the compounds selected from the group consisting of: (S)-6-oxo-piperidine-2-carboxylic acid ((S)-6-mercapto-1-phenylcarbamoyl-hexyl)-amide, (S)-6-oxo-piperidine-2-carboxylic acid ((S)-1-cyclopentylcarbamoyl-6-mercapto-hexyl)-amide, (S)-6-oxo-piperidine-2 carboxylic acid [(S)-1-(3-benzyloxy-benzylcarbamoyl)-6-mercapto-hexyl]amide, (S)-6-oxo-piperidine-2-carboxylic acid [(S)-6-mercapto-1-(4-trifluoromethyl-benzylcarbamoyl)-hexyl]-amide, (S)-4-oxo-azetidine-2-carboxylic acid ((S)-6-mercapto-1-phenylcarbamoyl-hexyl)-amide, (3S,4S)-2-oxo-4-phenyl-pyrrolidine-3 carboxylic acid ((S)-6-mercapto-1-phenylcarbamoyl-hexyl)-amide, (3R,4R)-2-oxo-4-phenyl-pyrrolidine-3-carboxylic acid ((S)-6-mercapto-1-phenylcarbamoyl-hexyl)amide, (3R,4S)-2-oxo-4-phenyl-pyrrolidine-3-carboxylic acid ((S)-6-mercapto-1-phenylcarbamoyl-hexyl)-amide, (3S,4R)-2-oxo-4-phenyl-pyrrolidine-3-carboxylic acid ((S)-6-mercapto-1-phenylcarbamoyl-hexyl)-amide, (S)-6-oxo-piperidine-2-carboxylic acid [(S)-1-(3,4-dihydro-1H-isoquinoline-2-carbonyl)-6-mercapto-hexyl]-amide, (R)-5-oxo-pyrrolidine-2-carboxylic acid ((S)-6-mercapto-1-phenylcarbamoyl-hexyl)-amide, (S)-6-oxo-piperidine-2-carboxylic acid [(S)-6-mercapto-1-(2-m-tolyl-ethylcarbamoyl)hexyl]-amide, (R)-2-oxo-piperidine-3-carboxylic acid ((S)-6-mercapto-1-phenylcarbamoyl-hexyl)-amide, (S)-2-oxo-piperidine-3-carboxylic acid ((S)-6-mercapto-1-phenylcarbamoyl-hexyl)-amide, (R)-6-oxo-piperidine-2-carboxylic acid ((S)-6-mercapto-1-phenylcarbamoyl-hexyl)-amide, (S)-6-oxo-1,2,3,6-tetrahydro-pyridine-2-carboxylic acid ((S)-6-mercapto-1-phenylcarbamoyl-hexyl)-amide, (S)-2-oxo-3-aza-bicyclo[4.1.0]heptane-4-carboxylic acid ((S)-6-mercapto-1-phenylcarbamoyl-hexyl)-amide, (S)-6-oxo-1,2,5,6-tetrahydro-pyridine-2-carboxylic acid ((S)-6-mercapto-1-phenylcarbamoyl-hexyl)-amide, (S)-4-oxo-3-aza-bicyclo[4.1.0]heptane-2-carboxylic acid ((S)-6-mercapto-1-phenylcarbamoyl-hexyl)amide, 6-oxo-1,6-dihydro-pyridine-2-carboxylic acid ((S)-6-mercapto-1-phenylcarbamoyl-hexyl)-amide, (S)-6-oxo-piperidine-2-carboxylic acid ((S)-5-mercapto-1-phenylcarbamoyl-pentyl)-amide, (S)-6-oxo-piperidine-2-carboxylic acid ((S)-7-mercapto-1-phenylcarbamoyl-heptyl)-amide, (S)-1-Methyl-6-oxo-piperidine-2 carboxylic acid ((S)-6-mercapto-1-phenylcarbamoyl-hexyl)-amide, (S)-6-Oxo-piperidine-2-carboxylic acid ((S)-6-mercapto-1-m-tolylcarbamoyl-hexyl)-amide, and (S)-6-Oxo-piperidine-2-carboxylic acid ((S)-6-mercapto-1-p-tolylcarbamoyl-hexyl)amide and the corresponding prodrugs wherein $R^3$ is as described for compounds of Formula (I) but is not H.

A still another embodiment of the present invention consists of the compounds selected from the group consisting of: thioacetic acid S—{(S)-6-[((S)-4-oxo-azetidine-2-carbonyl)-amino]-6-phenylcarbamoyl-hexyl}ester, thioacetic acid S—{(S)-6-[((S)-6-oxo-piperidine-2-carbonyl)-amino]-6-(4-trifluoromethyl-benzylcarbamoyl)-hexyl}ester, thioacetic acid S—{(S)-6-(3-benzyloxy-benzylcarbamoyl)-6-[((S)-6-oxo-piperidine-2-carbonyl)-amino]-hexyl}ester, thioacetic acid S—{(S)-7-(3,4-dihydro-1H-isoquinolin-2-yl)-7-oxo-6-[((S)-6-oxo-piperidine-2-carbonyl)-amino]-heptyl}ester, thioacetic acid S—[(S)-6-[((S)-6-oxo-piperidine-2-carbonyl)-amino]-6-(2-m-tolyl-ethylcarbamoyl)hexyl]ester, thioacetic acid S—{(S)-6-[((R)-6-oxo-piperidine-2-carbonyl)-amino]-6-phenylcarbamoyl-hexyl}ester, thioacetic acid S—{(S)-6-[((S)-6-oxo-piperidine-2-carbonyl)-amino]-6-phenylcarbamoyl-hexyl}ester, thioacetic acid S—{(S)-6-[((S)-6-oxo-piperidine-2-carbonyl)-amino]-6-p-tolylcarbamoyl-hexyl}ester, thioacetic acid S—{(S)-6-[((S)-6-oxo-piperidine-2-carbonyl)-amino]-6-m-tolylcarbamoyl-hexyl}ester, thioacetic acid S—{(S)-6-[((S)-6-oxo-piperidine-2-carbonyl)-amino]-6-cyclopentylcarbamoyl-hexyl}ester, thioacetic acid S—{(S)-6-[((3R*,4S*)-2-oxo-4-phenyl-pyrrolidine-3-carbonyl)-amino]-6- phenylcarbamoyl-hexyl}ester, thioacetic acid S—{(S)-6-[((3R*,4R*)-2-oxo-4-phenyl-pyrrolidine-3-carbonyl)-amino]-6-phenylcarbamoyl-hexyl}ester, thioacetic acid S—{(S)-6-[((R)-5-oxo-pyrrolidine-2-carbonyl)-amino]-6-phenylcarbamoyl-hexyl}ester, thioacetic acid S—{(S)-6-[(R*)-(2-oxo-piperidine-3-carbonyl)-amino]-6-phenyl carbamoyl-hexyl}ester, (S)-6-oxo-piperidine-2-carboxylic acid ((S)-6-mercapto-1-phenylcarbamoyl-hexyl)-amide, (S)-6-oxo-piperidine-2-carboxylic acid ((S)-1-cyclopentylcarbamoyl-6-mercapto-hexyl)amide, (S)-6-oxo-piperidine-2-carboxylic acid [(S)-1-(3-benzyloxy-benzylcarbamoyl)-6-mercapto-hexyl]-amide, (S)-6-oxo-piperidine-2-carboxylic acid [(S)-6-mercapto-1-(4-trifluoromethyl-benzylcarbamoyl)-hexyl]-amide, (S)-4-oxo-azetidine-2-carboxylic acid ((S)-6-mercapto-1-phenylcarbamoyl-hexyl)-amide, (3S,4S)-2-oxo-4-phenyl-pyrrolidine-3-carboxylic acid ((S)-6-mercapto-1-phenylcarbamoyl-hexyl)-amide, (3R,4R)-2-oxo-4-phenyl-pyrrolidine-3-carboxylic acid ((S)-6-mercapto-1-phenylcarbamoyl-hexyl)-amide, (3R,4S)-2-oxo-4-phenyl-pyrrolidine-3-carboxylic acid ((S)-6-mercapto-1-phenylcarbamoyl-hexyl)-amide, (3S,4R)-2-oxo-4-phenyl-pyrrolidine-3-carboxylic acid ((S)-6-mercapto-1-phenylcarbamoyl-hexyl)-amide, (S)-6-oxo-piperidine-2-carboxylic acid [(S)-1-(3,4-dihydro-1H-isoquinoline-2-carbonyl)-6-mercapto-hexyl]-amide, (R)-5-oxo-pyrrolidine-2-carb oxylic acid ((S)-6-mercapto-1-phenylcarbamoyl-hexyl)-amide, (S)-6-oxo-piperidine-2-carboxylic acid [(S)-6-mercapto-1-(2-m-tolyl-ethylcarbamoyl)-hexyl]-amide, (R)-2-oxo-piperidine-3-carboxylic acid ((S)-6-mercapto-1-phenylcarbamoyl-hexyl)-amide, (S)-2-oxo-piperidine-3-carboxylic acid ((S)-6-mercapto-1-phenylcarbamoyl-hexyl)-amide, (R)-6-oxo-piperidine-2-carboxylic acid ((S)-6-mercapto-1-phenylcarbamoyl-hexyl)-amide, thiocarbonic acid ethyl ester {(S)-6-[((S)-6-oxo-piperidine-2-carbonyl)-amino]-6-phenylcarbamoyl-hexyl}ester, thioisobutyric acid S—{(S)-6-[((S)-6-oxo-piperidine-2-carbonyl)-amino]-6-phenylcarbamoyl-hexyl}ester, thioacetic acid S—{(S)-6-[((S)-5-oxo-pyrrolidine-2-carbonyl)-amino]-6-phenylcarbamoyl-hexyl}ester, thioacetic acid S—{(S)-6-[((S)-5-oxo-pyrrolidine-2-carbonyl)-amino]-6-m-tolylcarbamoyl-hexyl}ester, thioacetic acid S—{(S)-6-[((R)-1-methyl-5-oxo-pyrrolidine-2-carbonyl)-amino]-6-phenylcarbamoyl-hexyl}ester, thiocarbonic acid ethyl ester {(S)-6-[((R)-5-oxo-pyrrolidine-2-carbonyl)-amino]-6-phenylcarbamoyl-hexyl}ester, thioacetic acid S—{(S)-6-[((R)-5-oxo-pyrrolidine-2-carbonyl)-amino]-6-m-tolylcarbamoyl-hexyl}ester, thioacetic acid S—{(S)-6-[((R)-1-methyl-5-oxo-pyrrolidine-2-carbonyl)-amino]-6-m-tolylcarbamoyl-hexyl}ester, thioacetic acid S—[(S)-6-[((R)-5-oxo-pyrrolidine-2-carbonyl)-amino]-6-(3-trifluoromethyl-phenylcarbamoyl)-hexyl]ester, thioacetic acid S—{(S)-6-[((S)-1-methyl-6-oxo-piperidine-2-carbonyl)-amino]-6-phenylcarbamoyl-hexyl}ester, (S)-1-methyl-6-oxo-piperidine-2-carboxylic acid ((S)-6-mercapto-1-phenylcarbamoyl-hexyl)-amide, (S)-6-oxo-piperidine-2-carboxylic acid ((S)-6-mercapto-1-m-tolylcarbamoyl-hexyl)-amide, (S)-6-oxo-piperidine-2-carboxylic acid ((S)-6-mercapto-1-p-tolylcarbamoyl-hexyl)-amide, and thioacetic acid S—{(S)-6-[((S)-6-oxo-1,2,3,6-tetrahydro-pyridine-2-carbonyl)-amino]-6-phenylcarbamoyl-hexyl}ester.

DESCRIPTION OF THE DRAWING

FIG. 1: Western Blot analysis of cytoplasmic and nuclear extracts of NCI-H460 cells after treatment with compound of Example 14.

The following illustrated examples are by no means an exhaustive list of what the present invention intends to protect.

EXAMPLES

Abbreviations

AcOEt: ethyl acetate

AIBN: azobisisobutyronitrile

DCM: dichloromethane

DIPEA: diisopropylethylamine

DMF: dimethylformamide

EDCI: 1-ethyl-3-(3-dimethylaminopropyl)-carbodiimide

EtOH: ethanol $Et_2O$: diethyl ether

HPLC: high-performance liquid chromatography

IPA: i-propyl alcohol

MeOH: methanol $NaHCO_3$: sodium bicarbonate $Na_2SO_4$: sodium sulphate $NEt_3$: triethylamine PyBOP: (benzotriazole-1-yl-oxy-tris-(dimethylamino)-phosphonium hexafluorophosphate)

RT: room temperature

SAc: thioacetyl

TFA: trifuoroacetic acid

TLC: thin layer chromatography

General Remarks:

All non-aqueous reactions were run in flame-dried glassware under a positive pressure of argon with exclusion of moisture from reagents and glassware using standard techniques for manipulating air-sensitive compounds. Anhydrous THF, toluene, $Et_2O$ and DCM were obtained by filtration through drying columns (Solvent Delivery System); other solvents were distilled under positive pressure of dry argon before use and dried by standard methods. Commercial grade reagents were used without further purification. Flash chromatography was performed on 230-400 mesh silica gel with the indicated solvent systems. Thin layer chromatography was performed on pre-coated, glass-backed silica gel plates (Merck 60$F_{254}$). Visualization was performed under short-wavelength ultraviolet light and/or by dipping the plates in an aqueous $H_2SO_4$ solution of cerium sulfate/ammonium molybdate, potassium permanganate, or ethanolic solution of anisaldehyde, followed by charring with a heat gun. Alternatively, TLC can be stained by exposing it to iodine vapour into a iodine development chamber. Low- and high-resolution mass analyses were performed on AEI-MS 902 or MS-50 spectrometers using electrospray (ES) techniques. Nuclear magnetic resonance spectra were recorded on Gemini spectrometers (Varian) at 300 or 500 MHz. Mass analyses were performed on Waters ZQ2000 spectrometer using electrospray (ES) technique. LCMS analyses were performed on a LC-Waters apparatus (HPLC Waters Alliance 2695, ZQ2000 MS and PDA-UV detector 2996).

Example 1

Thioacetic acid S—{(S)-6-[((S)-4-oxo-azetidine-2-carbonyl)-amino]-6-phenylcarbamoyl-hexyl}ester

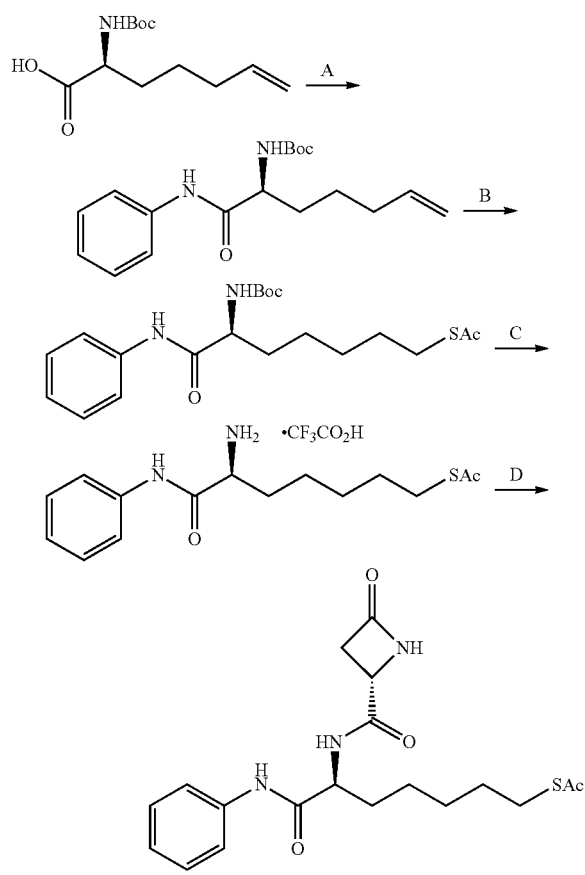

A: aniline, PyBOP, DIPEA, DMF and DCM, RT; B: AcSH, AIBN, dioxane, 75° C.; C: TFA, DCM, 0° C. to RT; D: (S)-4-oxo-azetidine-2-carboxylic acid, PyBOP, NEt₃, DMF and DCM, RT

Step A: ((S)-1-phenylcarbamoyl-hex-5-enyl)-carbamic acid tert-butyl ester

A solution of (S)-2-tert-butoxycarbonylamino-hept-6-enoic acid (5.24 mmol), DIPEA (15.7 mmol) and aniline (5.76 mmol) was stirred at RT in DCM (70 ml) for 20 minutes before adding PyBOP (5.24 mmol) and anhydrous DMF (5 ml). The reaction mixture was stirred for 2 hours at RT. The solvent was removed under reduced pressure and the crude reaction mixture was diluted with AcOEt, washed with 5% Na$_2$CO$_3$, water and then with 5% aqueous citric acid and finally with brine. After removal of the solvent under reduced pressure and purification on silica gel (n-hexane/AcOEt: 9/1) the desired adduct was obtained.

Yield: 85%.

$^1$H NMR (300 MHz, DMSO-d$_6$) δ: 1.13 (m, 2H), 1.14 (s, 9H), 1.60 (m, 2H), 2.01 (m, 2H), 4.05 (m, 1H), 4.94 (m, 2H), 5.77 (m, 1H), 7.02 (m, 2H), 7.29 (t, 2H), 7.59 (d, 2H), 9.92 (s, 1H).

ESIMS m/z 341.2 (M+Na)$^+$.

Step B: thioacetic acid S—((S)-6-tert-butoxycarbonylamino-6-phenylcarbamoyl-hexyl)ester To a stirred solution of ((S)-1-phenylcarbamoyl-hex-5-enyl)-carbamic acid tert-butyl ester (250 mg, 0.78 mmol), thioacetic acid (564 μl, 7.8 mmol) at 75° C. in degassed dioxane was added AIBN (129 mg, 0.78 mmol). The reaction mixture was stirred for 1 hour. The reaction mixture was cooled to 0° C. and an excess of cyclohexene was added under stirring, the latter being maintained for 20 mn. The reaction mixture was concentrated under reduced pressure, and the resulting crude product was rinsed more times with hexane to afford the desired adduct.

Yield: 81%.

$^1$H NMR (300 MHz, DMSO-d$_6$) δ: 1.30 (m, 4H), 1.36 (s, 9H), 1.47 (m, 2H), 1.56 (m, 2H), 2.29 (s, 3H), 2.79 (t, 2H), 4.02 (m, 1H), 6.96 (d, 1H), 7.02 (t, 1H), 7.28 (t, 2H), 7.57 (d, 2H), 9.89 (s, 1H).

ESIMS m/z 417.2 (M+Na)$^+$.

Step C: thioacetic acid S—((S)-6-amino-6-phenylcarbamoyl-hexyl) ester

To a stirred solution in DCM of thioacetic acid S—((S)-6-tert-butoxycarbonylamino-6-phenylcarbamoyl-hexyl) ester at 0° C. was added TFA slowly. The reaction mixture was then allowed to warm to RT and stirred overnight. The solvent was removed under reduced pressure to afford the desired adduct as the trifluoroacetate salt which was used without any purification in the next step.

Step D: thioacetic acid S—{(S)-6-[((S)-4-oxo-azetidine-2-carbonyl)-amino]-6-phenylcarbamoyl-hexyl}ester To a solution of the trifluoroacetate salt as obtained in step C (305 mg, 0.75 mmol) in DCM (10 ml), were added NEt$_3$ (312 μl, 2.24 mmol), (S)-4-oxo-azetidine-2-carboxylic acid (90 mg, 0.79 mmol), PyBOP (408 mg, 0.79 mmol) and DMF (1.7 ml). The reaction mixture was stirred overnight and then diluted with AcOEt, washed with water, 5% aq. Na$_2$CO$_3$, brine 5% citric acid solution and brine again. The crude material was purified through chromatography on silica gel using AcOEt as eluent to allow the desired adduct as a white solid.

Yield: 42%

$^1$H NMR (300 MHz, DMSO-d$_6$) δ: 1.31 (m, 4H), 1.48 (m, 2H), 1.64 (m, 2H), 2.29 (s, 3H), 2.67 (dt, 1H), 2.79 (t, 2H), 3.09 (dd, 1H), 4.06 (dd, 1H), 4.42 (m, 1H), 7.03 (t, 1H), 7.28 (t, 2H), 7.57 (d, 2H), 8.12 (s, 1H), 8.38 (d, 1H), 10.07 (s, 1H).

ESIMS m/z 392.0 (M+H)$^+$; ESIMS m/z 504.2 (M+CF$_3$COO)$^-$.

Examples 2 to 12 were synthesized following the procedure depicted in scheme 1 using the appropriate amine in step A and the adequate acid in step D.

Example 2

Thioacetic acid S—[(S)-6-[((S)-6-oxo-piperidine-2-carbonyl)-amino]-6-(4-trifluoromethyl-benzylcarbamoyl)-hexyl]ester Yield: 51%.

$^1$H NMR (500 MHz, CD$_2$Cl$_2$) δ: 1.39 (m, 4H), 1.56 (m, 2H), 1.64-1.94 (m, 5H), 2.05 (m, 1H), 2.24 (m, 2H), 2.32 (s, 3H), 2.84 (t, 2H), 4.00 (m, 1H), 4.46 (m, 3H), 7.21 (m, 1H), 7.32-7.47 (m, 4H), 7.60 (m, 2H).

ESIMS m/z 502.09 (M+H)$^+$.

Example 3

Thioacetic acid S—{(S)-6-(3-benzyloxy-benzylcarbamoyl)-6-[((S)-6-oxo-piperidine-2-carbonyl)-amino]-hexyl}ester Yield: 44%.
$^1$H NMR (500 MHz, CD$_2$Cl$_2$) δ: 1.25-1.48 (m, 4H), 1.56 (m, 2H), 1.62-1.97 (m, 5H), 2.01 (m, 1H), 2.23 (m, 2H), 2.30 (s, 3H), 2.83 (t, 2H), 3.98 (m, 1H), 4.36 (m, 2H), 4.46 (m, 1H), 5.06 (m, 2H), 6.82-6.92 (m, 3H), 7.02 (m, 1H), 7.25 (t, 1H), 7.32-7.50 (m, 5H).
ESIMS m/z 540.17 (M+H)$^+$.

Example 4

Thioacetic acid S—{(S)-7-(3,4-dihydro-1H-isoquinolin-2-yl)-7-oxo-6-[((S)-6-oxo-piperidine-2-carbonyl)-amino]-heptyl}ester Yield: 28%.
$^1$H NMR (500 MHz, DMSO-d$_6$) δ: 1.15-1.85 (m, 13H), 2.11 (m, 2H), 2.29 (s, 3H), 2.79 (m, 3H), 3.69 (m, 2H), 3.91 (m, 1H), 4.45-4.90 (m, 3H), 7.16 (s, 4H) 7.47 (m, 1H), 8.10 (m, 1H).
ESIMS m/z 460.14 (M+H)$^+$.

Example 5

Thioacetic acid S—[(S)-6-[((S)-6-oxo-piperidine-2-carbonyl)-amino]-6-(2-m-tolyl-ethylcarbamoyl)-hexyl]ester Yield: 27%.
$^1$H NMR (500 MHz, DMSO-d$_6$) δ: 1.06-1.32 (m, 4H), 1.36-1.76 (m, 7H), 1.76-1.88 (m, 1H), 2.10 (t, 2H), 2.26 (s, 3H), 2.30 (s, 3H), 2.65 (t, 2H), 2.78 (t, 2H), 3.21 (m, 2H), 3.89 (m, 1H), 4.16 (m, 1H), 6.93-7.03 (m, 2H), 7.14 (m, 1H), 7.50 (d, 1H), 7.86-8.00 (m, 3H).
ESIMS m/z 462.11 (M+H)$^+$.

Example 6

Thioacetic acid S—{(S)-6-[((R)-1-methyl-5-oxo-pyrrolidine-2-carbonyl)-amino]-6-m-tolylcarbamoyl-hexyl}ester Yield: 37%.
$^1$H NMR (300 MHz, DMSO-d$_6$) δ: 1.31 (m, 4H), 1.48 (m, 2H), 1.63 (m, 2H), 1.80 (m, 1H), 2.17 (m, 3H), 2.25 (s, 3H), 2.28 (s, 3H), 2.58 (s, 3H), 2.80 (t, 2H), 4.13 (m, 1H), 4.37 (m, 1H), 6.85 (d, 1H), 7.16 (t, 1H), 7.36 (d, 1H), 7.40 (s, 1H), 8.47 (d, 1H), 9.99 (s, 1H).
ESIMS m/z 433.4 (M+H)$^+$; 546.5 (M+CF$_3$COO)$^-$.

Example 7

Thioacetic acid S—{(S)-6-[((S)-5-oxo-pyrrolidine-2-carbonyl)-amino]-6-m-tolylcarbamoyl-hexyl}ester Yield: 53%.
$^1$H NMR (300 MHz, DMSO-d$_6$) δ: 1.33 (m, 4H), 1.50 (m, 2H), 1.65 (m, 2H), 1.88 (m, 1H), 2.11 (m, 2H), 2.25 (m, 1H), 2.27 (s, 3H), 2.31 (s, 3H), 2.81 (t, 2H), 4.10 (m, 1H), 4.38 (m, 1H), 6.87 (d, 1H), 7.18 (t, 1H), 7.37 (d, 1H), 7.42 (s, 1H), 7.79 (s, 1H), 8.19 (d, 1H), 9.96 (s, 1H).
ESIMS m/z 420.3 (M+H)$^+$.

Example 8

Thioacetic acid S—{(S)-6-[((R)-5-oxo-pyrrolidine-2-carbonyl)-amino]-6-m-tolylcarbamoyl-hexyl}ester Yield: 43%.
$^1$H NMR (300 MHz, DMSO-d$_6$) δ: 1.30 (m, 4H), 1.48 (m, 2H), 1.64 (m, 2H), 1.84 (m, 1H), 2.10 (m, 2H), 2.25 (m, 1H), 2.25 (s, 3H), 2.28 (s, 3H), 2.79 (t, 2H), 4.09 (m, 1H), 4.39 (m, 1H), 6.85 (d, 1H), 7.16 (t, 1H), 7.36 (d, 1H), 7.40 (s, 1H), 7.80 (s, 1H), 8.15 (d, 1H), 9.96 (s, 1H).
ESIMS m/z 420.3 (M+H)$^+$.

Example 9

Thioacetic acid S—{(S)-6-[((R)-1-methyl-5-oxo-pyrrolidine-2-carbonyl)-amino]-6-phenylcarbamoyl-hexyl}ester Yield: 36%.
$^1$H NMR (300 MHz, DMSO-d$_6$) δ: 1.34 (m, 4H), 1.51 (m, 2H), 1.66 (m, 2H), 1.82 (m, 1H), 2.22 (m, 3H), 2.31 (s, 3H), 2.61 (s, 3H), 2.82 (t, 2H), 4.14 (m, 1H), 4.42 (m, 1H), 7.07 (t, 1H), 7.32 (t, 2H), 7.60 (d, 2H), 8.47 (d, 1H), 10.10 (s, 1H).
ESIMS m/z 420.3 (M+H)$^+$.

Example 10

Thioacetic acid S—{(S)-6-[((S)-6-oxo-1,2,3,6-tetrahydro-pyridine-2-carbonyl)-amino]-6-phenylcarbamoyl-hexyl}ester Yield: 64%.
$^1$H NMR (300 MHz, DMSO-d$_6$) δ: 1.28 (m, 4H), 1.45 (m, 2H), 1.65 (m, 2H), 2.28 (s, 3H), 2.55 (m, 2H), 2.78 (t, 2H), 4.08 (m, 1H), 4.38 (m, 1H), 5.66 (m, 1H), 6.50 (m, 1H), 7.03 (t, 1H), 7.28 (t, 2H), 7.47 (m, 1H), 7.56 (d, 2H), 8.02 (d, 1H), 10.10 (s, 1H).
ESIMS m/z 440.1 (M+Na)$^+$.

Example 11

Thioacetic acid S—{(S)-6-[((S)-5-oxo-pyrrolidine-2-carbonyl)-amino]-6-phenylcarbamoyl-hexyl}ester Yield: 25%.
$^1$H NMR (300 MHz, DMSO-d$_6$) δ: 1.32 (m, 4H), 1.48 (m, 2H), 1.63 (m, 2H), 1.87 (m, 1H), 2.08 (m, 2H), 2.22 (m, 2H), 2.30 (s, 3H), 2.79 (t, 2H), 4.09 (m, 1H), 4.38 (m, 1H), 7.03 (t, 1H), 7.28 (t, 2H), 7.58 (d, 1H), 7.78 (s, 1H), 8.20 (d, 1H), 10.03 (s, 1H).
ESIMS m/z 406.4 (M+H)$^+$.

Example 12

Thioacetic acid S—{(S)-6-[((S)-1-methyl-6-oxo-piperidine-2-carbonyl)-amino]-6-phenylcarbamoyl-hexyl}ester Yield: 68%.
$^1$H NMR (300 MHz, DMSO-d$_6$) δ: 1.32 (m, 4H), 1.48 (m, 2H), 1.58 (m, 2H), 1.68 (m, 2H), 1.86 (m, 2H), 2.17 (m, 2H), 2.29 (s, 3H), 2.68 (s, 3H), 2.79 (t, 2H), 4.07 (m, 1H), 4.43 (m, 1H), 7.03 (t, 1H), 7.28 (t, 2H), 7.58 (d, 2H), 8.35 (d, 1H), 10.07 (s, 1H).
ESIMS m/z 433.9 (M+H)$^+$.

Example 13

Thioacetic acid S—{(S)-6-[((R)-6-oxo-piperidine-2-carbonyl)-amino]-6-phenylcarbamoyl-hexyl}ester

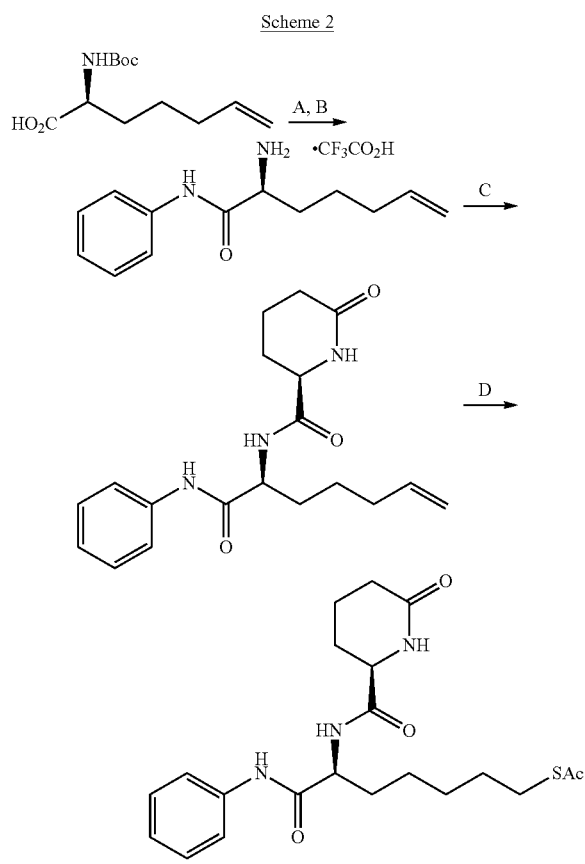

Scheme 2

A: aniline, PyBOP, DIPEA, DMF and DCM, RT; B: TFA, DCM, 0° C. to RT; C: (R)-6-oxo-piperidine-2-carboxylic acid, PyBOP, NEt₃, DMF and DCM, RT; D: AcSH, AIBN, dioxane, 75° C.

Step A: ((S)-1-phenylcarbamoyl-hex-5-enyl)-carbamic acid tert-butyl ester

The compound has been obtained following Step A as described in example 1.

Step B: (S)-2-amino-hept-6-enoic acid phenylamide

To a stirred solution of ((S)-1-phenylcarbamoyl-hex-5-enyl)-carbamic acid tert-butyl ester (i.e., example 1, Step A) at 0° C. was added TFA slowly. The reaction mixture was then allowed to warm to RT and stirred for 2 hours. The solvent was removed under reduced pressure to afford the desired adduct quantitatively as the trifluoroacetate salt which was used without any purification in the next step.

Step C: (R)-6-oxo-piperidine-2-carboxylic acid ((S)-1-phenylcarbamoyl-hex-5-enyl)amide A solution of DCM/DMF (10 ml, 10/2) of the trifluoroacetate salt obtained in Step A was reacted with (R)-6-oxo-piperidine-2-carboxylic acid (0.79 mmol) and PyBOP (0.79 mmol) in the presence of NEt₃ (2.25 mmol) for 2 hours. The reaction mixture was diluted with DCM and washed with 5% $Na_2CO_3$, brine, 5% citric acid and brine. The organic phase was dried over $Na_2SO_4$, filtered and concentrated under reduced pressure. The crude reaction mixture was purified through chromatography on silica gel using AcOEt/MeOH (9/1) as eluent to allow the desired adduct as a white solid.

Yield: 85%

$^1$H NMR (300 MHz, DMSO-$d_6$) δ: 1.38 (m, 2H), 1.65 (m, 5H), 1.86 (m, 1H), 2.03 (m, 2H), 2.11 (t, 2H), 3.96 (m, 1H), 4.44 (m, 1H), 4.96 (m, 2H), 5.77 (m, 1H), 7.04 (t, 1H), 7.29 (t, 2H), 7.47 (d, 1H), 7.57 (d, 2H), 8.13 (d, 1H), 10.03 (s, 1H).

ESIMS m/z 366.3 (M+Na)⁺; 342.2 (M–H)⁻.

Step D: Thioacetic acid S—{(S)-6-[((R)-6-oxo-piperidine-2-carbonyl)-amino]-6-phenylcarbamoyl-hexyl}ester To a stirred solution of (R)-6-oxo-piperidine-2-carboxylic acid ((S)-1-phenylcarbamoyl-hex-5-enyl)-amide (220 mg, 0.64 mmol), thioacetic acid (460 μl, 6.4 mmol) at 75° C. in degassed dioxane (7 ml) was added AIBN (105 mg, 0.64 mmol). The reaction mixture was stirred until complete conversion of the starting material as monitored by TLC analysis. The reaction mixture was cooled to 0° C. and quenched with an excess of cyclohexene under stirring, the latter being maintained for 20 minutes. Concentration under reduced pressure and purification through chromatography on silica gel using Hexane/DCM/IPA: 50/40/10 as eluent afforded the desired adduct.

Yield: 53%.

$^1$H NMR (300 MHz, DMSO-$d_6$) δ: 1.30 (m, 4H), 1.47 (m, 2H), 1.64 (m, 5H), 1.86 (m, 1H), 2.11 (t, 2H), 2.29 (s, 3H), 2.79 (t, 2H), 3.95 (m, 1H), 4.41 (m, 1H), 7.03 (t, 1H), 7.29 (t, 2H), 7.48 (d, 1H), 7.57 (d, 2H), 8.14 (d, 1H), 10.05 (s, 1H).

ESIMS m/z 420.1 (M+H)⁺; 532.2 (M+CF₃COO)⁺.

Examples 14 to 18 were synthesized following the procedure depicted in scheme 2 using the appropriate amine in step A and the adequate acid in step C.

Example 14

Thioacetic acid S—{(S)-6-[((S)-6-oxo-piperidine-2-carbonyl)-amino]-6-phenylcarbamoyl-hexyl}ester Yield: 87%.

$^1$H NMR (200 MHz CDCl₃) δ: 1.31 (m, 4H), 1.47 (m, 2H), 1.64 (m, 5H), 1.84 (m, 1H), 2.09 (t, 2H), 2.29 (s, 3H), 2.79 (t, 2H), 3.95 (m, 1H), 4.37 (m, 1H), 7.03 (t, 1H), 7.28 (t, 2H), 7.47 (d, 1H), 7.57 (d, 2H), 8.08 (d, 1H), 9.97 (s, 1H). ESIMS m/z 420.0 (M+H)⁺; 532.2 (M+CF₃COO)⁻.

Example 15

Thioacetic acid S—{(S)-6-[((S)-6-oxo-piperidine-2-carbonyl)-amino]-6-p-tolylcarbamoyl-hexyl}ester Yield: 88%.

$^1$H NMR (300 MHz, DMSO-$d_6$) δ: 1.30 (m, 2H), 1.47 (m, 2H), 1.64 (m, 5H), 1.84 (m, 1H), 2.10 (t, 2H), 2.23 (s, 3H), 2.29 (s, 3H), 2.79 (t, 2H), 3.94 (m, 1H), 4.37 (m, 1H), 7.09 (d, 2H), 7.45 (d, 2H), 7.47 (d, 1H), 8.06 (d, 1H), 9.87 (s, 1H).

ESIMS m/z 456.6 (M+H)⁺.

Example 16

Thioacetic acid S—{(S)-6-[((S)-6-oxo-piperidine-2-carbonyl)-amino]-6-m-tolylcarbamoyl-hexyl}ester Yield: 62%.

$^1$H NMR (300 MHz, DMSO-$d_6$) δ: 1.31 (m, 4H), 1.47 (m, 2H), 1.61 (m, 5H), 1.84 (m, 1H), 2.10 (t, 2H), 2.25 (s, 3H), 2.29 (s, 3H), 2.80 (t, 2H), 3.95 (m, 1H), 4.36 (m, 1H), 6.85 (d, 1H), 7.16 (t, 1H), 7.35 (d, 1H), 7.40 (s, 1H), 7.47 (d, 1H), 8.09 (d, 1H), 9.90 (s, 1H).
ESIMS m/z 456.4 (M+H)⁺.

Example 17

Thioacetic acid S—{(S)-6-[((S)-6-oxo-piperidine-2-carbonyl)-amino]-6-cyclopentylcarbamoyl-hexyl}ester Yield: 51%.
¹H NMR (500 MHz, DMSO-d₆) δ: 1.05-1.90 (m, 20H), 2.10 (t, 2H), 2.30 (s, 3H), 2.80 (t, 2H), 3.95 (m, 2H), 4.20 (m, 1H), 7.50 (d, 1H), 7.80 (s, 1H), 7.82 (s, 1H).
ESIMS m/z 434.38 (M+Na)⁺.

Example 18

Thioacetic acid S—[(S)-6-[((R)-5-oxo-pyrrolidine-2-carbonyl)-amino]-6-(3-trifluoromethyl-phenylcarbamoyl)-hexyl]ester Yield: 84%.
¹H NMR (300 MHz, DMSO-d₆) δ: 1.31 (m, 4H), 1.48 (m, 2H), 1.66 (m, 2H), 1.84 (m, 1H), 2.28 (s, 3H), 2.25 (m, 1H), 2.10 (m, 2H), 2.79 (t, 2H), 4.09 (m, 1H), 4.37 (m, 1H), 7.39 (d, 1H), 7.54 (t, 1H), 7.77 (d, 1H), 7.80 (s, 1H), 8.08 (s, 1H), 8.26 (d, 1H), 10.43 (s, 1H).
¹⁹F NMR (282 MHz, DMSO-d₆) δ: −62.97
ESIMS m/z 474.3 (M+H)⁺; 586.3 (M+CF₃COO)⁻.

Example 19

Thioacetic acid S—{(S)-6-[((3R*,4S*)-2-oxo-4-phenyl-pyrrolidine-3-carbonyl)-amino]-6-phenylcarbamoyl-hexyl}ester Scheme 3

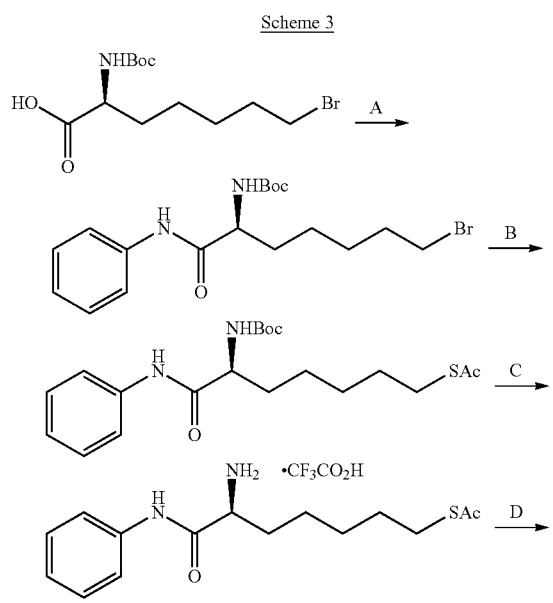

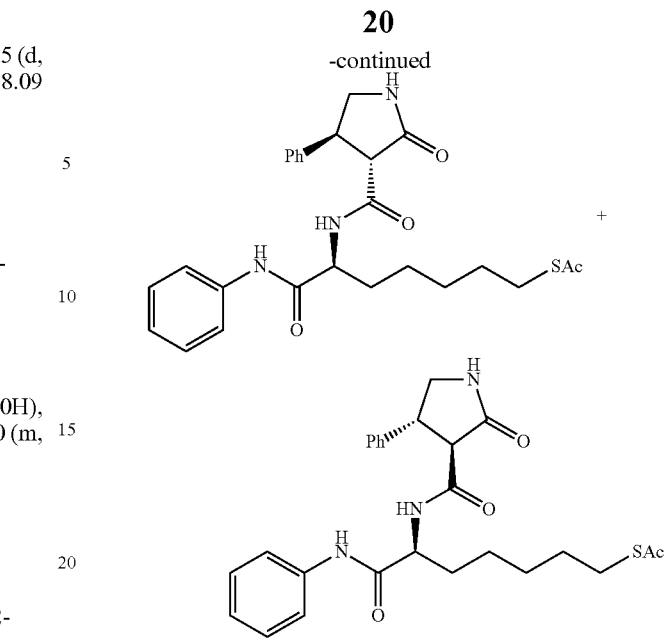

A: PhNH₂, EDCl, HOBT, RT; B: KSAc, EtOH, RT; C: TFA, DCM, RT; D: (3R*,4S*)-2-oxo-4-phenyl-pyrrolidine-3-carboxylic acid, PyBOP, DIPEA, RT; E: NaOH, EtOH, RT Step A: ((S)-6-bromo-1-phenylcarbamoyl-hexyl)-carbamic acid tert-butyl ester EDCI (2.10 g, 11.1 mmol) and aniline (0.68 ml, 7.5 mmol) were added to a solution of 7.4 mmol of (S)-7-bromo-2-tert-butoxycarbonylamino-heptanoic acid (Gupta P. K., et al., Bioorg. Med. Chem. Lett., 2010, 20, 23, 7067) in THF (70 ml) and the reaction mixture was stirred overnight at RT. The solvent was removed under reduced pressure and the crude reaction mixture was diluted with AcOEt, washed with water and then with 10% aqueous citric acid and finally with saturated NaHCO₃. After removal of the solvent under reduced pressure and purification on silica gel (n-hexane/AcOEt: 1/9) the desired adduct was obtained.
Yield: 91%.
¹H NMR (500 MHz, CDCl₃) δ: 1.38-1.48 (m, 14H), 1.75-2.00 (m, 3H), 3.48 (t, 2H), 4.30 (m, 1H), 5.40 (m, 1H), 6.50 (m, 1H), 7.12 (t, 1H), 7.33 (t, 2H), 7.60 (d, 2H).
ESIMS m/z 421.21 (M+Na)⁺; 423.21 (M+Na)⁺.

Step B: thioacetic acid S—((S)-6-tert-butoxycarbonylamino-6-phenylcarbamoyl-hexyl) ester Potassium thioacetate (9.7 mmol) was added to a solution of ((S)-6-bromo-1-phenylcarbamoyl-hexyl)-carbamic acid tert-butyl ester (6.5 mmol) in EtOH (40 ml). The reaction mixture was stirred at RT overnight. The solvent was removed under reduced pressure and the resulting precipitate was poured into water and extracted twice with AcOEt. The organic layer was washed with brine and dried over Na₂SO₄ before being evaporated to afford the desired adduct.
Yield: 97%
¹H NMR (300 MHz, CDCl₃) δ: 1.45-1.50 (m, 13H) 1.65-1.55 (m, 3H), 2.10 (t, 3H), 2.74 (m, 1H), 2.84 (t, 2H), 4.17 (s, 1H), 5.04 (s, 1H), 7.10 (t, 1H), 7.30 (t, 1H), 7.52 (d, 2H).
ESIMS m/z 417.41 (M+Na)⁺.

Step C: thioacetic acid S—((S)-6-amino-6-phenylcarbamoyl-hexyl) ester-trifluoroacetate Trifuoroacetic acid (61 mmol) was added to a solution of thioacetic acid S—((S)-6-tert-butoxycarbonylamino-6-phenylcarbamoyl-hexyl) ester (6.10 mmol) in DCM (30 ml). The reaction mixture was stirred at RT for five hours before being concentrated under reduced pressure. The resulting crude reaction mixture was taken up twice in Et$_2$O to enable complete removal of the excess of trifluoroacetic acid. The desired adduct was obtained as a reddish oil.

Yield: quantitative $^1$H NMR (500 MHz, DMSO-d$_6$) δ: 1.20-2.00 (m, 8H), 2.31 (s, 3H), 2.80 (t, 2H), 4.05 (m, 1H), 7.05 (t, 1H), 7.30 (t, 2H), 7.40 (m, 3H), 7.58 (d, 2H), 9.85 (s, 1H).

Step D: thioacetic acid S—{(S)-6-[(2-oxo-4-phenyl-pyrrolidine-3-carbonyl)-amino]-6-phenylcarbamoyl-hexyl}ester Thioacetic acid S—((S)-6-amino-6-phenylcarbamoyl-hexyl) ester-trifluoroacetate (1.03 mmol), DIPEA (3.08 mmol) and PyBOP (1.03 mmol) were added to a solution of (3R*,4S*)-2-oxo-4-phenyl-pyrrolidine-3-carboxylic acid in DCM/DMF: 5/9. The resulting reaction mixture was stirred at RT overnight. After removal of the solvent under reduced pressure, the resulting solid was poured into water and extracted twice with AcOEt. The organic layer was then washed with NaHCO$_3$, water and brine before being dried over Na$_2$SO$_4$ and concentrated under reduced pressure to yield an oil. The latter was partially purified by silica gel chromatography and then subjected to HPLC purification.

Yield: 12%.

$^1$H NMR (500 MHz, Acetone-d$_6$) δ: 1.30-1.80 (m, 8H), 2.28 (s, 3H), 2.81 (t, 2H), 3.51 (t, 1H), 3.75 (d, 1H), 3.87 (m, 1H), 4.31 (m, 1H), 4.54 (m, 1H), 7.00-7.40 (m, 8H), 7.53 (bs, 1H), 7.84 (m, 2H), 7.89 (d, 1H), 9.80 (bs, 1H).

ESIMS m/z 482.06 (M+H)$^+$.

Examples 20 to 22 were synthesized following the procedure depicted in scheme 3 using the appropriate amine in step A and the adequate acid in step D.

Example 20

Thioacetic acid S—{(S)-6-[((3R*,4R*)-2-oxo-4-phenyl-pyrrolidine-3-carbonyl)-amino]-6-phenylcarbamoyl-hexyl}ester In step D the reacting acid was the cis racemic (i.e., "3R*, 4R*") mixture of 2-oxo-4-phenyl-pyrrolidine-3-carboxylic acid.

Yield: 60%.

$^1$H NMR (300 MHz, Acetone-d$_6$) δ: 1.35-2.00 (m, 8H), 2.28 (s, 3H), 2.84 (t, 2H), 3.40 (t, 1H), 3.59 (d, 1H), 3.78 (m, 1H), 4.13 (m, 1H), 4.48 (m, 1H), 7.00-7.40 (m, 9H), 7.63 (m, 2H), 7.89 (d, 1H), 9.25 (bs, 1H).

ESIMS m/z 482.06 (M+H)$^+$.

Example 21

Thioacetic acid S—{(S)-6-[((R)-5-oxo-pyrrolidine-2-carbonyl)-amino]-6-phenylcarbamoyl-hexyl}ester Yield: 35%.

$^1$H NMR (500 MHz, CD$_3$OD) δ: 1.20-2.00 (m, 10H), 2.18 (m, 2H), 2.29 (s, 3H), 2.80 (t, 2H), 4.07 (m, 1H), 4.40 (m, 1H), 7.04 (t, 2H), 7.29 (t, 2H), 7.57 (d, 1H), 7.58 (d, 2H), 8.10 (d, 1H), 9.90 (s, 1H).

ESIMS m/z 428.17 (M+Na)$^+$.

Example 22

Thioacetic acid S—{(S)-6-[(R*)-(2-oxo-piperidine-3-carbonyl)-amino]-6-phenyl carbamoyl-hexyl}ester Yield: 60%.

$^1$H NMR (500 MHz, CD$_3$OD) δ: 1.42-1.19 (m, 10H), 2.29 (s, 3H), 2.55 (t, 2H), 2.80 (t, 2H), 3.35 (m, 2H), 3.40 (m, 2H), 4.53 (m, 2H), 7.12 (t, 1H), 7.33 (t, 2H), 7.60 (d, 2H).

ESIMS m/z 442.14 (M+Na)$^+$.

Example 23

(S)-6-Oxo-piperidine-2-carboxylic acid ((S)-6-mercapto-1-phenylcarbamoyl-hexyl)amide

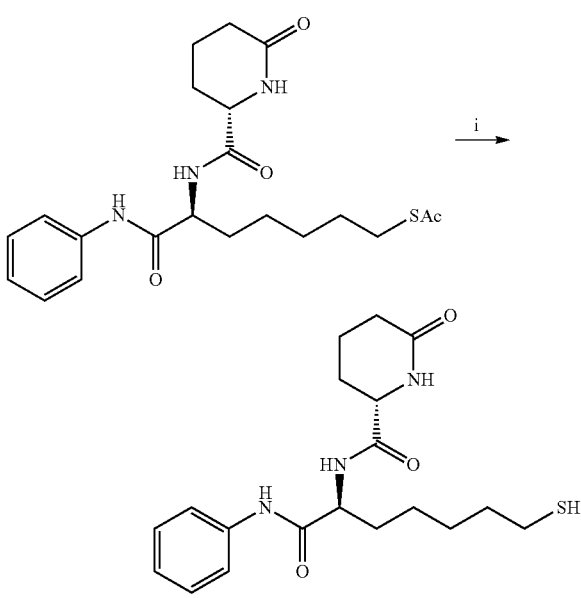

Scheme 4 i: NaOH, EtOH, RT

A 2N solution of NaOH (7.0 mmol) was added to a solution of thioacetic acid S—{(S)-6-[((S)-6-oxo-piperidine-2-carbonyl)-amino]-6-phenylcarbamoyl-hexyl}ester (0.95 mmol) in EtOH (13 ml). The reaction mixture was stirred at RT overnight and then poured into water and extracted with AcOEt, washed with water, brine and finally dried over Na$_2$SO$_4$. Removal of the solvent under reduced pressure led to the desired adduct, which was purified through HPLC.

Yield: 20%.

$^1$H NMR (500 MHz, CD$_3$OD) δ: 1.50 (m, 4H), 1.68 (m, 2H), 1.80 (m, 2H), 1.95 (m, 3H), 2.10 (m, 1H), 2.38 (m, 2H), 2.55 (t, 2H), 4.15 (t, 1H), 4.53 (m, 1H), 7.12 (t, 1H), 7.33 (t, 2H), 7.60 (d, 2H).

ESIMS m/z 400.40 (M+Na)$^+$; 376.34 (M−H)$^-$.

Examples 24 to 40 were synthesized following the procedure depicted in scheme 4 using the appropriate starting material.

Example 24

(S)-6-Oxo-piperidine-2-carboxylic acid ((S)-1-cyclopentylcarbamoyl-6-mercapto-hexyl)amide Starting material was the one of example 17.
Yield: 44%.
$^1$H NMR (500 MHz, DMSO-d$_6$) δ: 1.05-1.90 (m, 20H), 2.12 (t, 2H), 2.21 (t, 1H), 2.45 (m, 2H), 3.92 (m, 1H), 3.97 (m, 1H), 4.21 (m, 1H), 7.55 (d, 1H), 7.80 (s, 1H), 7.82 (s, 1H).
ESIMS m/z 392.2 (M+Na)$^+$; 368.1 (M−H)$^−$.

Example 25

(S)-6-Oxo-piperidine-2-carboxylic acid [(S)-1-(3-benzyloxy-benzylcarbamoyl)-6-mercapto-hexyl]-amide Starting material was the one of example 3.
Yield: 32%.
$^1$H NMR (500 MHz, CD$_2$C$_{12}$) δ: 1.20-1.48 (m, 4H), 1.48-2.02 (m, 8H), 2.21 (m, 2H), 2.49 (m, 2H), 3.20-3.42 (m, 2H), 4.51 (m, 1H), 5.04 (s, 2H), 6.80-6.95 (m, 3H), 7.23 (t, 1H), 7.28-7.50 (m, 5H), 7.64 (s, 1H), 7.75 (d, 1H).
ESIMS m/z 498.35 (M+H)$^+$.

Example 26

(S)-6-Oxo-piperidine-2-carboxylic acid [(S)-6-mercapto-1-(4-trifluoromethyl-benzylcarbamoyl)-hexyl]-amide Starting material was the one of example 2.
Yield: 33%.
$^1$H NMR (500 MHz, CD$_2$Cl$_2$) δ: 1.38 (m, 4H), 1.52-2.12 (m, 9H), 2.23 (m, 2H), 2.50 (m, 2H), 3.98 (m, 1H), 4.45 (m, 3H), 7.20 (m, 1H), 7.28-7.72 (m, 6H).
ESIMS m/z 460.14 (M+H)$^+$.

Example 27

(S)-4-Oxo-azetidine-2-carboxylic acid ((S)-6-mercapto-1-phenylcarbamoyl-hexyl)amide Starting material was the one of example 1.
Yield: 56%.
$^1$H NMR (300 MHz, DMSO-d$_6$) δ: 1.34 (m, 4H), 1.57 (m, 4H), 2.22 (t, 1H), 2.47 (q, 1H), 2.66 (m, 2H), 3.10 (dd, 1H), 4.07 (m, 1H), 4.43 (m, 1H), 7.04 (t, 1H), 7.29 (t, 2H), 7.58 (d, 2H), 8.15 (s, 1H), 8.43 (d, 1H), 10.11 (s, 1H).
ESIMS m/z 372.2 (M+Na)$^+$; 348.2 (M−H)$^−$.

Example 28

(3S,4S)-2-Oxo-4-phenyl-pyrrolidine-3-carboxylic acid ((S)-6-mercapto-1-phenylcarbamoyl-hexyl)-amide Starting material was the one of example 20. Once hydrolysed, the diastereomeric mixture of the two thiolate derivatives was purified by flash chromatography on silica gel to allow the obtention of each pure isomer.
Yield: 44%.
$^1$H NMR (500 MHz, Acetone-d$_6$) δ: 1.35-2.00 (m, 8H), 2.42 (t, 2H), 3.40 (t, 1H), 3.59 (d, 1H), 3.78 (m, 1H), 4.13 (m, 1H), 4.48 (m, 1H), 7.00-7.40 (m, 9H), 7.63 (m, 2H), 7.89 (d, 1H), 9.25 (bs, 1H).
ESIMS m/z 462.27 (M+Na)$^+$.

Example 29

(3R,4R)-2-Oxo-4-phenyl-pyrrolidine-3-carboxylic acid ((S)-6-mercapto-1-phenylcarbamoyl-hexyl)-amide Example 29 was obtained after purification according to procedure of example 28.
Yield: 37%.
$^1$H NMR (500 MHz, Acetone-d$_6$) δ: 1.35-2.00 (m, 8H), 2.42 (t, 2H), 3.51 (t, 1H), 3.75 (d, 1H), 3.87 (m, 1H), 4.31 (m, 1H), 4.54 (m, 1H), 7.00-7.40 (m, 9H), 7.63 (m, 2H), 7.89 (d, 1H), 9.25 (bs, 1H).
ESIMS m/z 462.27 (M+Na)$^+$.

Example 30

(3R,4S)-2-Oxo-4-phenyl-pyrrolidine-3-carboxylic acid ((S)-6-mercapto-1-phenylcarbamoyl-hexyl)-amide Starting material was the one of example 19. Once hydrolysed, the diastereomeric mixture of the two thiolate derivatives was purified by flash chromatography on silica gel to allow the obtention of the pure isomer.
Yield: 40%.
$^1$H NMR (500 MHz, Acetone-d$_6$) δ: 1.30-1.80 (m, 8H), 2.42 (t, 2H), 3.51 (t, 1H), 3.75 (d, 1H), 3.87 (m, 1H), 4.31 (m, 1H), 4.54 (m, 1H), 7.00-7.40 (m, 8H), 7.53 (bs, 1H), 7.84 (m, 2H), 7.89 (d, 1H), 9.80 (bs, 1H).
ESIMS m/z 462.81 (M+Na)$^+$.

Example 31

(3S,4R)-2-Oxo-4-phenyl-pyrrolidine-3-carboxylic acid ((S)-6-mercapto-1-phenylcarbamoyl-hexyl)-amide Example 31 was obtained after purification according to procedure of example 30.
Yield: 37%.
$^1$H NMR (500 MHz, CD$_3$OD) δ: 1.35-2.40 (m, 8H), 2.43 (m, 2H), 3.48 (t, 1H), 3.80 (m, 2H), 4.22 (m, 1H), 4.53 (m, 1H), 7.09 (m, 2H), 7.30 (m, 4H), 7.36 (m, 4H), 7.68 (m, 2H).
ESIMS m/z 462.27 (M+Na)$^+$.

Example 32

(S)-6-Oxo-piperidine-2-carboxylic acid [(S)-1-(3,4-dihydro-1H-isoquinoline-2-carbonyl)-6-mercapto-hexyl]-amide Starting material was the one of example 4.
Yield: 37%.
$^1$H NMR (500 MHz, DMSO-d$_6$) δ: 1.10-1.90 (m, 13H), 2.05-2.23 (m, 2H), 2.35-3.00 (m, 4H), 3.60-4.10 (m, 3H), 4.48-4.86 (m, 3H), 7.17 (s, 4H), 7.49 (m, 1H), 8.10 (m, 4H).
ESIMS m/z 418.05 (M+H)$^+$.

Example 33

(R)-5-Oxo-pyrrolidine-2-carboxylic acid ((S)-6-mercapto-1-phenylcarbamoyl-hexyl)amide Starting material was the one of example 21.
Yield: 42%.
$^1$H NMR (500 MHz, DMSO-d$_6$) δ: 1.20-2.00 (m, 10H), 2.18 (m, 2H), 2.21 (t, 1H), 2.45 (m, 1H), 4.05 (m, 1H), 4.40 (m, 1H), 7.04 (t, 1H), 7.29 (t, 2H), 7.55 (d, 1H), 7.58 (d, 2H), 8.08 (d, 1H), 9.98 (s, 1H).
ESIMS m/z 364.28 (M+H)$^+$.

Example 34

(S)-6-Oxo-piperidine-2-carboxylic acid [(S)-6-mercapto-1-(2-m-tolyl-ethylcarbamoyl)hexyl]-amide Starting material was the one of example 5.
Yield: 41%.
$^1$H NMR (500 MHz, DMSO-d$_6$) δ: 1.10-1.34 (m, 4H), 1.42-1.76 (m, 7H), 1.83 (m, 1H), 2.11 (t, 2H), 2.21 (t, 1H), 2.27 (s, 3H), 2.44 (m, 2H), 2.66 (t, 2H), 3.23 (m, 2H), 3.91 (m, 1H), 4.19 (m, 1H), 6.90-7.08 (m, 2H), 7.16 (t, 1H), 7.51 (bs, 1H), 7.89 (d, 1H), 7.95 (t, 1H).
ESIMS m/z 420.09 (M+H)$^+$.

Example 35

(R)-2-Oxo-piperidine-3-carboxylic acid ((S)-6-mercapto-1-phenylcarbamoyl-hexyl)amide Starting material was the one of example 22. Once hydrolysed, the diastereomeric mixture of the two thiolate derivatives was purified by flash chromatography on silica gel to allow the obtention of the pure isomer.
Yield: 39%.
$^1$H NMR (500 MHz, CD$_3$OD) δ: 1.42-1.19 (m, 12H), 2.55 (t, 2H), 3.35 (m, 2H), 3.40 (m, 2H), 4.53 (m, 2H), 7.12 (t, 1H), 7.33 (t, 2H), 7.60 (d, 2H).
ESIMS m/z 400.40 (M+Na)$^+$.

Example 36

(S)-2-Oxo-piperidine-3-carboxylic acid ((S)-6-mercapto-1-phenylcarbamoyl-hexyl)amide Example 36 was obtained after purification according to procedure of example 35.
Yield: 20%.
$^1$H NMR (500 MHz, CD$_3$OD) δ: 1.40-2.22 (m, 12H), 2.55 (t, 2H), 3.35 (m, 2H), 3.42 (m, 2H), 4.53 (m, 2H), 7.09 (t, 1H), 7.29 (t, 2H), 7.68 (d, 2H).
ESIMS m/z 400.40 (M+Na)$^+$.

Example 37

(R)-6-Oxo-piperidine-2-carboxylic acid ((S)-6-mercapto-1-phenylcarbamoyl-hexyl)amide Starting material was the one of example 13.
Yield: 82%.
$^1$H NMR (300 MHz, DMSO-d$_6$) δ: 1.34 (m, 4H), 1.51 (m, 2H), 1.64 (m, 5H), 1.87 (m, 1H), 2.11 (t, 2H), 2.22 (t, 1H), 2.44 (m, 2H), 3.96 (m, 1H), 4.43 (m, 1H), 7.04 (t, 1H), 7.29 (t, 2H), 7.49 (d, 1H), 7.57 (d, 2H), 8.13 (d, 1H), 10.04 (s, 1H).
ESIMS m/z 400.2 (M+Na)$^+$; 376.2 (M–H)$^-$.

Example 38

(S)-6-Oxo-piperidine-2-carboxylic acid ((S)-6-mercapto-1-m-tolylcarbamoyl-hexyl)amide Starting material was the one of example 16.
Yield: 25%.
$^1$H NMR (300 MHz, DMSO-d$_6$) δ: 1.34 (m, 4H), 1.51 (m, 2H), 1.64 (m, 5H), 1.85 (m, 1H), 2.10 (t, 2H), 2.20 (t, 1H) 2.25 (s, 3H), 2.44 (m, 2H), 3.95 (m, 1H), 4.38 (m, 1H), 6.85 (d, 1H), 7.16 (t, 1H), 7.36 (d, 1H), 7.41 (s, 1H), 7.48 (d, 1H), 8.06 (d, 1H), 9.89 (s, 1H).
ESIMS m/z 414.3 (M+Na)$^+$; 390.4 (M–H)$^-$.

Example 39

(S)-6-Oxo-piperidine-2-carboxylic acid ((S)-6-mercapto-1-p-tolylcarbamoyl-hexyl)amide Starting material was the one of example 15.
Yield: 53%.
$^1$H NMR (300 MHz, DMSO-d$_6$) δ: 1.33 (m, 4H), 1.51 (m, 2H), 1.60 (m, 5H), 1.83 (m, 1H), 2.10 (t, 2H), 2.21 (t, 1H), 2.23 (s, 3H), 2.43 (m, 2H), 3.95 (m, 1H), 4.37 (m, 1H), 7.09 (d, 2H), 7.45 (d, 2H), 7.48 (d, 1H), 8.08 (d, 1H), 9.89 (s, 1H).
ESIMS m/z 414.4 (M+Na)$^+$; 390.3 (M–H)$^-$.

Example 40

(S)-1-Methyl-6-oxo-piperidine-2-carboxylic acid ((S)-6-mercapto-1-phenylcarbamoyl-hexyl)-amide Starting material was the one of example 12.
Yield: 28%.
$^1$H NMR (300 MHz, DMSO-d$_6$) δ: 1.34 (m, 4H), 1.49 (m, 2H), 1.57 (m, 3H), 1.66 (m, 2H), 1.88 (m, 2H), 2.17 (m, 2H), 2.67 (s, 3H), 2.80 (t, 2H), 4.08 (m, 1H), 4.42 (m, 1H), 7.02 (t, 1H), 7.26 (t, 2H), 7.56 (d, 2H), 8.33 (d, 1H), 10.05 (s, 1H).
ESIMS m/z 392.0 (M+H)$^+$.

Example 41

Thiocarbonic acid ethyl ester {(S)-6-[((S)-6-oxo-piperidine-2-carbonyl)-amino]-6-phenylcarbamoyl-hexyl}ester To a solution of (S)-6-oxo-piperidine-2-carboxylic acid ((S)-6-mercapto-1-phenylcarbamoyl-hexyl)-amide (0.21 mmol) in DCM (20 ml) were added NEt$_3$ (0.23 mmol) and ethylchloroformate (0.23 mmol). The reaction mixture was stirred at RT for 2 hours. The reaction mixture was concentrated under reduced pressure and the crude product was purified through chromatography on silica gel using AcOEt/MeOH: 80/20 as eluent.
Yield: 74%.
$^1$H NMR (500 MHz, DMSO-d$_6$) δ: 1.20 (t, 3H), 1.25-1.45 (m, 4H), 1.52-1.80 (m, 7H), 1.87 (m, 1H), 2.11 (t, 2H), 2.82 (t, 2H), 3.97 (m, 1H), 4.21 (m, 4H), 3.47 (q, 2H), 4.41 (m, 1H), 7.05 (t, 1H), 7.30 (t, 2H), 7.48 (bs, 1H), 7.58 (d, 2H), 8.10 (d, 1H), 9.99 (s, 1H).
ESIMS m/z 450.15 (M+H)$^+$.

Example 42 was synthesized following the procedure of example 41 using the (R)-5-oxo-pyrrolidine-2-carboxylic acid ((S)-6-mercapto-1-phenylcarbamoyl-hexyl)-amide instead of (S)-6-oxo-piperidine-2-carboxylic acid ((S)-6-mercapto-1-phenylcarbamoyl-hexyl)-amide.

Example 42

Thiocarbonic acid ethyl ester {(S)-6-[((R)-5-oxo-pyrrolidine-2-carbonyl)-amino]-6-phenylcarbamoyl-hexyl}ester Yield: 82%.
$^1$H NMR (300 MHz, DMSO-$d_6$) δ: 1.18 (t, 3H), 1.33 (m, 4H), 1.6 (m, 4H), 1.85 (m, 1H), 2.10 (m, 2H), 2.25 (m, 1H), 2.79 (t, 2H), 4.09 (m, 1H), 4.20 (q, 2H), 4.42 (m, 1H), 7.03 (t, 1H), 7.28 (t, 2H), 7.57 (d, 2H), 7.82 (s, 1H), 8.20 (d, 1H), 10.05 (s, 1H).
ESIMS m/z 436.3 (M+H)$^+$.

Example 43

Thioisobutyric acid S—{(S)-6-[((S)-6-oxo-piperidine-2-carbonyl)-amino]-6-phenylcarbamoyl-hexyl}ester This compound was synthesised following the procedure described for example 30 but using isobutyryl chloride instead of ethylchloroformate.
Yield: 42%.
$^1$H NMR (500 MHz, DMSO-$d_6$) δ: 1.04 (t, 6H), 1.22-1.44 (m, 4H), 1.46-1.77 (m, 6H), 1.93 (m, 1H), 2.06 (m, 1H), 2.20 (m, 1H), 2.37 (m, 1H), 2.48 (m, 4H), 3.47 (m, 1H), 4.32 (m, 1H), 4.81 (m, 1H), 7.04 (t, 1H), 7.29 (t, 2H), 7.57 (d, 2H), 8.33 (d, 1H), 9.99 (s, 1H).
ESIMS m/z 448.24 (M+H)$^+$.

Biology

Example 44

HDAC Enzymatic Assay

HDAC profiling was performed against eleven HDAC isolated human isoforms in the presence of the fluorogenic tetrapeptide RHKKAc (from p53 residues 379-382) substrate (10 μM). Isolated human HDACs were be obtained by standard purification, with the exception of HDAC3 which was a human recombinant protein as a complex of full length human HDAC3 with a C-terminal His-tag and human NCOR2 amino acids 395-489 with an N-terminal GST-tag co-expressed in baculovirus expression system. Each compound was dissolved in DMSO, and progressively diluted solutions were used for testing. TSA and SAHA were used as reference compounds. Upon its deacetylation, the fluorophore was released given rise to fluorescence emission which was detected by a fluorimeter, and the IC$_{50}$ values of the compounds were determined by analyzing dose-response inhibition curves. TSA and SAHA were used as reference compounds.

TABLE 1

| Examples | HDAC isoforms IC$_{50}$ (nM) | | | | | | | | | | |
|---|---|---|---|---|---|---|---|---|---|---|---|
|  | 1 | 2 | 3 | 4 | 5 | 6 | 7 | 8 | 9 | 10 | 11 |
| SAHA | + | + | + | + | + | +++ | + | + | + | + | + |
| 23 | +++ | ++ | +++ | +++ | +++ | +++ | +++ | + | +++ | +++ | +++ |
| 24 | + | + | ++ | +++ | + | +++ | +++ | + | +++ | + | ++ |
| 25 | + | + | + | + | + | ++ | + | +++ | + | + | + |
| 26 | + | + | + | +++ | + | + | + | +++ | + | + | + |
| 27 | +++ | ++ | +++ | + | +++ | +++ | +++ | ++ | +++ | +++ | +++ |
| 28 | +++ | + | +++ | +++ | ++ | +++ | + | + | +++ | +++ | +++ |
| 29 | ++ | + | ++ | +++ | + | +++ | + | + | ++ | +++ | +++ |
| 30 | ++ | + | ++ | +++ | + | + | + | + | ++ | +++ | +++ |
| 31 | +++ | +++ | +++ | +++ | +++ | +++ | +++ | +++ | +++ | +++ | +++ |
| 32 | + | +++ | + | +++ | + | + | + | + | + | + | + |
| 33 | +++ | ++ | +++ | ++ | +++ | +++ | +++ | + | +++ | +++ | +++ |
| 34 | ++ | + | + | +++ | + | +++ | + | +++ | + | ++ | ++ |
| 35 | +++ | +++ | +++ | +++ | +++ | +++ | +++ | ++ | +++ | +++ | +++ |
| 36 | +++ | +++ | +++ | +++ | +++ | +++ | ++ | + | +++ | +++ | +++ |
| 37 | +++ | +++ | +++ | +++ | +++ | +++ | + | + | +++ | +++ | +++ |
| 38 | +++ | +++ | +++ | + | +++ | +++ | +++ | + | +++ | +++ | +++ |
| 39 | +++ | ++ | +++ | + | +++ | +++ | +++ | + | +++ | +++ | +++ |
| 40 | +++ | ++ | +++ | + | +++ | +++ | +++ | + | +++ | +++ | +++ |

IC$_{50}$ < 50 nM: +++;
50 nM < IC$_{50}$ < 100 nM: ++;
100 nM < IC$_{50}$ < 500 nM: +

Compound A

Thioacetic acid S-(6-phenylcarbamoyl-hexyl)ester

This commercially available derivative which does not present the lactam-carbonylamino moiety on the side chain of the scaffold was tested as a comparison example in an in vivo experiment involving compound of example 14 (table 8).

Results

The compounds of the present invention proved to be highly potent on all HDAC isoforms with inhibitory activity ranging in the low nanomolar scale (Table 1). Such a finding was surprising in the light of the biological behaviour of the comparison derivative (i.e., ((S)-1-cyclopentylcarbamoyl-6-mercapto-hexyl)-carbamic acid tert-butyl ester and reported in Itoh Y., et al., *J. Med. Chem.*, 2007, 50, 5425). Indeed, as previously reported, we verified and confirmed its HDAC6 selectivity profile finding moreover a much lower activity on HDAC6 than most of the herein described compounds.

When comparing the HDAC inhibitory profile of some of the above derivatives with the one of corresponding hydroxamate analogues, we surprisingly found that the former thio derivatives were at least equipotent or even more potent than the hydroxamate zinc-binding group containing analogues (Table 2).

TABLE 2

| Examples | MBG | HDAC isoforms |||||||||||
|---|---|---|---|---|---|---|---|---|---|---|---|---|
| | | 1 | 2 | 3 | 4 | 5 | 6 | 7 | 8 | 9 | 10 | 11 |
| 21 | SH | +++ | ++ | +++ | +++ | +++ | +++ | +++ | + | +++ | +++ | +++ |
| | CONHOH | +++ | ++ | +++ | + | ++ | +++ | +++ | ++ | +++ | ++ | +++ |
| 31 | SH | +++ | +++ | +++ | +++ | +++ | +++ | +++ | +++ | +++ | +++ | +++ |
| | CONHOH | +++ | + | +++ | + | ++ | +++ | ++ | + | +++ | ++ | ++ |
| 33 | SH | +++ | ++ | +++ | ++ | +++ | +++ | +++ | + | +++ | +++ | +++ |
| | CONHOH | +++ | + | ++ | + | ++ | +++ | + | + | ++ | ++ | ++ |

$IC_{50} < 50$ nM: +++;
50 nM $< IC_{50} <$ 100 nM: ++;
100 nM $< IC_{50} <$ 500 nM: +

Example 45

Cytotoxicity

The cytotoxic effect of some compounds of the present invention on NCI-H460 non-small cell lung carcinoma was and HCT116 colon cancer cells was evaluated according to the method of Skehan et al. (Skehan P., et al., *J. Natl. Cancer Inst.*, 1990, 82, 13, 1107), and using SAHA (Vorinostat) as reference compound.

Tumour cells were grown in RPMI 1640 medium containing 10% heat-inactivated foetal bovine serum and 50 µg/ml gentamycin sulphate and were seeded in 96-well tissue culture plates at approximately 10% confluence. They were allowed to attach and recover for at least 24 h. Varying concentrations of the compounds of the present invention were then added to each well in order to define their $IC_{50}$ value (i.e., the concentration which inhibits 50% of cell survival).

The plates were incubated for 24 h at 37° C., after which they were washed 3 times by removal of the supernatant and addition of PBS. The plates were then incubated for further 48 h at 37° C. 200 µl PBS and 50 µl of cold 80% TCA were added and the plates were incubated on ice for at least 1 h. TCA was removed and the plates were washed 3 times by immersion in distilled-water. They were then dried on paper at 40° C. for 5 min. 200 µl of 0.4% sulphorodamine B in 1% acetic acid were added. The plates were incubated at room temperature for further 30 min. Sulphorodamine B was removed, and the plates were washed 3 times by immersion in 1% acetic acid and were dried on paper and at 40° C. for 5 min. Then 200 µl Tris 10 mM were added. The plates were kept under magnetic stirring for 20 min. Cell survival was determined by means of optical density by a Multiskan spectrofluorimeter at 540 nm. The amount of cells killed was calculated as the percentage decrease in sulphorodamine B binding compared to control cultures. The $IC_{50}$ values (reported in Table 3 for H460 cell line and in Table 4 for HCT116 cell line) were calculated with the "ALLFIT" program.

Results

The compounds of the present invention demonstrated a very good inhibition profile, very often much better than that observed for the reference compound SAHA.

TABLE 3

| H460 cell line ||
|---|---|
| Example | $IC_{50}$ (µM) |
| SAHA | + |
| 1 | +++ |
| 5 | + |

TABLE 3-continued

| H460 cell line ||
|---|---|
| Example | $IC_{50}$ (µM) |
| 6 | +++ |
| 7 | +++ |
| 8 | +++ |
| 10 | +++ |
| 11 | +++ |
| 13 | +++ |
| 14 | +++ |
| 15 | +++ |
| 16 | +++ |
| 18 | +++ |
| 19 | +++ |
| 21 | +++ |
| 41 | ++ |
| 42 | +++ |
| 43 | + |

$IC_{50} < 0.5$ µM: +++;
0.5 µM $< IC_{50} <$ 1.0 µM: ++;
1.0 µM $< IC_{50} <$ 10 µM: +

TABLE 4

| HCT116 cell line ||
|---|---|
| Example | $IC_{50}$ (µM) |
| SAHA | + |
| 14 | +++ |
| 17 | + |
| 19 | +++ |
| 20 | ++ |
| 22 | + |
| 31 | + |
| 33 | + |

$IC_{50} < 0.5$ µM: +++;
0.5 µM $< IC_{50} <$ 1.0 µM: ++;
1.0 µM $< IC_{50} <$ 10 µM: +

Example 46

Compound of example 21 was further investigated on an extended panel of cell lines in order to assess its cytotoxicity in comparison with SAHA used as reference compound.

Tumour cells (A2780, SKOV-3, MDA-MB436, MCF-7, HSC3) in adhesion were grown in RPMI 1640 medium containing 10% heat-inactivated foetal bovine serum and 50 μg/ml of gentamycin sulphate, meanwhile DMEM was used for MDA-MB231 cell line. Cells were seeded in 96-well tissue culture plates at approximately 10% confluence. They were allowed to attach and recover for at least 24 h. Compounds of the present invention were then added to each well at various concentrations in order to define cell survival inhibition $IC_{50}$. The plates were incubated for 72 h at 37° C., after which time they were washed 3 times by removal of the supernatant. 200 μl of PBS and 50 μl of cold 80% TCA were added and the plates were incubated on ice for at least 1 h. TCA was removed and the plates were washed 3 times by immersion in distilled water. They were then dried on paper at 40° C. for 5 min. 200 μl of 0.4% sulphorodamine B in 1% acetic acid were added. The plates were incubated at room temperature for further 30 min. Sulphorodamine B was removed, and the plates were washed 3 times by immersion in 1% acetic acid and were dried on paper at 40° C. for 5 min. Then 200 μl Tris 10 mM were added. The plates were kept under magnetic stirring for 20 min. Cell survival was determined by means of optical density by a Multiskan spectrofluorimeter at 540 nm. The amount of cells killed was calculated as the percentage decrease in sulphorodamine B binding compared to control cultures. The $IC_{50}$ values (reported in Table 5) were calculated with the "ALLFIT" program.

U937, HUT78 and K562 were grown in suspension in RPMI 1640 medium containing 10% heat inactivated foetal bovine serum and 50 μg/ml of gentamycin sulphate, meanwhile MV4-11 cells were grown in Iscove's modified Dulbecco's medium. The experimental procedure was as described above except that removal of the supernatant was made by means of centrifugation of the plates at 1600×g for 10 min (operation effected twice).

Results are reported in Table 5.

TABLE 5

| Tumour cell lines | | Drugs tested $IC_{50}$ (μM) | |
|---|---|---|---|
| Cancer Type | Cells Type | Example 14 | SAHA |
| ovarian | A2780 | 0.062 | 1.71 |
|  | SKOV-3 | 0.38 | 5.7 |
| breast | MDA-MB231 | 0.23 | 1.41 |
|  | MDA-MB436 | 0.18 | 1.71 |
|  | MCF-7 | 0.19 | 2.55 |
| head and neck | HSC3 | 0.77 | 8.6 |
| acute monocytic leukemia | MV4-11 | 0.19 | 2.1 |
| T-Lymphoma | U937 | 0.049 | 0.071 |
|  | HUT78 | 0.48 | 1.5 |
| chronic myeloid leukemia | K562 | 0.19 | 0.13 |

Results reported in table 5 explicitly demonstrate that compound of example 14 is endowed of potent anti-cancer properties on a wild panel of cell lines meanwhile the comparison compound SAHA generally demonstrated a generally much lower biological activity.

Example 47

Tubulin and Histone Acetylation

Western Blot analysis of cytoplasmic and nuclear extracts of NCI-H460 cells which had been previously incubated with compound of example 14 or SAHA, was conducted to measure α-tubulin and histone acetylation, using various antibodies as reported underneath:

mouse anti-acetyl-tubulin monoclonal antibody (Sigma; cat. T6793);

mouse anti-β-actin monoclonal antibody (Sigma; cat. A5316);

rabbit anti-acetyl-Histone H4 polyclonal antibody (Upstate; cat. 06-598);

mouse anti-Histone H4 monoclonal antibody (Upstate; cat. 07-108).

The experiments were conducted using ECL Plus Western blotting detection reagents (from Amersham Biosciences) and the intensity of the bands were analyzed by using a computed phosphoimage analyzer (PhosphoImager; Molecular Dynamics, Sunnyvale, Calif., U.S.A.).

Results

Compound of example 14 demonstrated to induce a hyperacetylation of cytoplasmatic α-tubulin comparable to that observed with the reference compound SAHA. Moreover, compound of example 14 also induced H4 hyper-acetylation at a concentration as low as 100 nM, meanwhile SAHA was 6 fold less effective in inducing histone H4 acetylation (i.e., FIG. 1 and Table 6).

TABLE 6

| Compound | $EC_{50}$ μM H4 acetylation |
|---|---|
| Example 14 | 0.1 |
| SAHA | 0.6 |

Example 48

Antitumour Activity

HCT116 colon cancer cells, or NCI-H460 NSCLC, or H929 multiple myeloma cells, all suspended in 0.1 ml of Medium 199, were inoculated subcutaneously (s.c.) in the right flank of CD1 nude mice (i.e., 5×10$^6$ for HCT116; 3×10$^6$ for NCI-H460 and 20×10$^6$ for H929). Treatments (i.e., as reported in table 6) started three days after tumour injection according to the schedule qd×5/w×3w with the exception of cisplatin which was given q4d/w×3w. The tested derivatives were administered as a suspension in PBS/DMSO/Cremophor EL (Sigma): 85/10/5 (volume percentage). The antitumour activity was determined by measuring tumour diameters with a Vernier calliper according to the Formula $$TV = d^2 \times D/2$$

where d and D are the shortest and longest diameters, respectively.

When tumours reached a volume of about 1000 mm$^3$, mice were sacrificed by cervical dislocation. The efficacy of the drug was assessed as the tumour volume inhibition according to the Formula reported underneath:

$$TVI\ \% = 100 - \left[\left(\frac{\text{mean } TV \text{ of treated group}}{\text{mean } TV \text{ of control group}}\right) \times 100\right]$$

Body weight recording was carried out to evaluate body weight loss as calculated in the equation underneath:

$$\% \ BWL = 100 - \left[\frac{BW_{day_x}}{BW_{day1}}\right] \times 100$$

Wherein BW day x corresponds to the mean weight at day x of the experiment meanwhile BW day 1 corresponds to the mean weight at the first day of the experiment.

Results

Compound of example 14 showed a comparable or even superior tumour volume inhibition at a dose three folds inferior to that SAHA in the three experiments. Treatments were also well supported by all the animals (Table 7).

TABLE 7

| Xenograft | Drugs | Dose (mg/10 ml/kg) | TVI % | BWL % |
|---|---|---|---|---|
| HCT116 | SAHA | 100 p.o. | 47 | 0 |
|  | Example 14 | 50 i.p. | 44 | 3 |
| NCI-H460 | SAHA | 100 i.p. | 27 | 0 |
|  | Example 14 | 50 i.p. | 36 | 2 |
|  | Cisplatin | 2 i.p. | 56 | 3 |
|  | Example 14 + cisplatin | 50 i.p. + 2 i.p. | 74 | 15 |
| H929 | SAHA | 100 i.p. | 21 | 3 |
|  | Example 14 | 50 i.p. | 30 | 11 |

Example 49

Antitumour Activity

The experiment of example 48 was repeated with another compound on mice animal model developing HCT116 colon cancer as described above or A2780 ovarian cancer, and administering the drugs solubilised in orally in PEG200/DMSO/Cremophor EL (Sigma): 85/10/5 (volume percentage). The results are reported in table 8.

TABLE 8

| Xenograft | Drugs | Dose (mg/10 ml/kg) | TVI % | BWL % |
|---|---|---|---|---|
| HCT116 | SAHA | 100 p.o. | 32 | 1 |
|  | Example 21 | 60 p.o. | 62 | 1 |
|  | Compound A | 100 p.o. | 11 | 0 |
| A2780 | SAHA | 100 p.o. | 53 | 4 |
|  | Example 21 | 110 p.o. | 89 | 7 |

Compound of example 21 demonstrated a potent biological activity affront of its analogue Compound A which is deprived of the side-chain, thus demonstrating the importance of the lactam-carbonylamino moiety of the scaffold. Moreover, compound of example 21 also showed strong biological activity in an ovarian cancer animal model with a TVI superior to that engendered by SAHA. It is also important to note that even after oral administration, a potent biological activity was found suggesting a high stability to first pass metabolism.

The invention claimed is:

1. A compound having the general Formula (I)

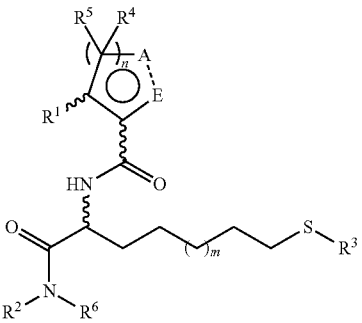

Formula I wherein,
$R^1$ is H, $(C_1-C_6)$-alkyl or aryl; or alternatively
$R^1$ and one $R^4$, each being linked to two adjacent carbon atoms, in case n is 2 or 3, are taken together to form a cyclopropane ring;
$R^2$ is phenyl optionally substituted with halogen, benzyloxy, $(C_1-C_3)$-alkyl or $CF_3$; $(C_3-C_6)$-cycloalkyl; aryl-$(C_1-C_6)$-alkyl wherein the aryl is optionally substituted with benzyloxy, $(C_1-C_3)$-alkyl or $CF_3$;
$R^3$ is H, $PO(OH)_2$, or a group of Formula (II)

—(CO)—$R^7$    Formula II $R^7$ is $(C_1-C_7)$-alkyl, $(C_1-C_6)$-alkoxy or —$CH(NH_2)R^8$;
$R^8$ is H, or the side chain of a natural α-amino acid in all possible isomeric forms and selected from the group consisting of glycine, alanine, phenylalanine, valine, leucine, isoleucine, aspartic acid, asparagine, glutamic acid, glutamine, serine, lysine, histidine, methionine, proline, cysteine, threonine, tryptophan, arginine and tyrosine;
$R^4$ and $R^5$ are at any occurrence independently H, halogen, $(C_1-C_6)$-alkyl, or alternatively, when n is 2 or 3, one $R^4$ and one $R^5$, each being linked to two adjacent carbon atoms, are taken together to form a cyclopropane ring;
$R^6$ is H or alternatively,
$R^2$ and $R^6$ are taken together to form a five- to six-membered heterocycle which can be optionally fused with an aryl moiety;
-A-E- is —(CO)—(NR$^9$)— or —(NR$^9$)—(CO)—;
$R^9$ is H or $(C_1-C_3)$-alkyl;
m is an integer comprised between 0 to 3;
n is an integer comprised between 0 to 3 with the proviso that when is 2 or 3, each of $R^4$ and $R^5$ can adopt different meaning at each occurrence;
the symbol ⌇ means that the carbon atom bearing said symbol can adopt a R or S configuration;
the symbol ○ can be absent, but if present it means that the cycle can be partially unsaturated with the proviso that when the carbon atom bearing $R^4$ is involved in a double bond, $R^5$ is absent;
their tautomers, their geometrical isomers, their optically active forms and their racemate forms, as well as their pharmaceutically acceptable salts thereof.

2. A compound according to claim 1, wherein n is 1 or 2.
3. A compound according to claim 1, wherein m is 1 or 2.
4. A compound according to claim 1, wherein said optically active forms are enantiomers and diastereomers.

5. A pharmaceutical composition containing a compound according to claim 1 as the active ingredient in mixtures with a pharmaceutically acceptable vehicle and/or excipient.

6. A method for the treatment of a pathological state selected from the group consisting of cancer disease consisting of ovarian, breast, colon, head and neck, acute monocytic leukemia, T-Lymphoma, chronic myeloid leukemia and non-small cell lung cancer, comprising administering an effective amount of a compound of claim 1 to a patient in need thereof.

7. Method according to claim 6 where the cancer is a metastatic form of cancer.

8. The method of claim 6, wherein the effective amount is from 0.01 mg/kg to 100 mg/kg.

9. The method of claim 8, wherein the effective amount is from 0.05 mg/kg to 50 mg/kg.

10. Process for synthesizing compounds of claim 1, by reacting compounds of Formula (III)

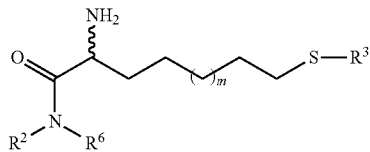

Formula III wherein $R^2$, $R^3$ and $R^6$ and m are as described in claim 1, with compounds of Formula (IV) salified or not

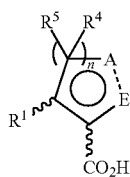

Formula IV wherein $R^1$, $R^4$ and $R^5$ and n are as described in claim 1, in a polar aprotic solvent in the presence of a coupling agent.

11. A compound according to claim 1 selected from the group consisting of:
thioacetic acid S—{(S)-6-[((S)-4-oxo-azetidine-2-carbonyl)-amino]-6-phenylcarbamoyl-hexyl}ester,
thioacetic acid S—[(S)-6-[((S)-6-oxo-piperidine-2-carbonyl)-amino]-6-(4-trifluoromethyl-benzylcarbamoyl)-hexyl]ester,
thioacetic acid S—{(S)-6-(3-benzyloxy-benzylcarbamoyl)-6-[((S)-6-oxo-piperidine-2-carbonyl)-amino]-hexyl}ester,
thioacetic acid S—{(S)-7-(3,4-dihydro-1H-isoquinolin-2-yl)-7-oxo-6-[((S)-6-oxo-piperidine-2-carbonyl)-amino]-heptyl}ester,
thioacetic acid S—[(S)-6-[((S)-6-oxo-piperidine-2-carbonyl)-amino]-6-(2-m-tolyl-ethylcarbamoyl)-hexyl]ester,
thioacetic acid S—{(S)-6-[((R)-6-oxo-piperidine-2-carbonyl)-amino]-6-phenylcarbamoyl-hexyl}ester, thioacetic acid S—{(S)-6-[((S)-6-oxo-piperidine-2-carbonyl)-amino]-6-phenylcarbamoyl-hexyl}ester,
thioacetic acid S—{(S)-6-[((S)-6-oxo-piperidine-2-carbonyl)-amino]-6-p-tolylcarbamoyl-hexyl}ester,
thioacetic acid S—{(S)-6-[((S)-6-oxo-piperidine-2-carbonyl)-amino]-6-m-tolylcarbamoyl-hexyl}ester,
thioacetic acid S—{(S)-6-[((S)-6-oxo-piperidine-2-carbonyl)-amino]-6-cyclopentylcarbamoyl-hexyl}ester,
thioacetic acid S—{(S)-6-[((3R*,4S*)-2-oxo-4-phenyl-pyrrolidine-3-carbonyl)-amino]-6-phenylcarbamoyl-hexyl}ester,
thioacetic acid S—{(S)-6-[((3R*,4R*)-2-oxo-4-phenyl-pyrrolidine-3-carbonyl)-amino]-6-phenylcarbamoyl-hexyl}ester,
thioacetic acid S—{(S)-6-[((R)-5-oxo-pyrrolidine-2-carbonyl)-amino]-6-phenylcarbamoyl-hexyl}ester,
thioacetic acid S—{(S)-6-[(R*)-(2-oxo-piperidine-3-carbonyl)-amino]-6-phenyl carbamoyl-hexyl}ester,
(S)-6-oxo-piperidine-2-carboxylic acid ((S)-6-mercapto-1-phenylcarbamoyl-hexyl)-amide,
(S)-6-oxo-piperidine-2-carboxylic acid ((S)-1-cyclopentylcarbamoyl-6-mercapto-hexyl)-amide,
(S)-6-oxo-piperidine-2-carboxylic acid [(S)-1-(3-benzyloxy-benzylcarbamoyl)-6-mercapto-hexyl]-amide,
(S)-6-oxo-piperidine-2-carboxylic acid [(S)-6-mercapto-1-(4-trifluoromethyl-benzylcarbamoyl)-hexyl]-amide,
(S)-4-oxo-azetidine-2-carboxylic acid ((S)-6-mercapto-1-phenylcarbamoyl-hexyl)-amide,
(3S,4S)-2-oxo-4-phenyl-pyrrolidine-3-carboxylic acid ((S)-6-mercapto-1-phenylcarbamoyl-hexyl)-amide,
(3R,4R)-2-oxo-4-phenyl-pyrrolidine-3-carboxylic acid ((S)-6-mercapto-1-phenylcarbamoyl-hexyl)-amide,
(3R,4S)-2-oxo-4-phenyl-pyrrolidine-3-carboxylic acid ((S)-6-mercapto-1-phenylcarbamoyl-hexyl)-amide,
(3S,4R)-2-oxo-4-phenyl-pyrrolidine-3-carboxylic acid ((S)-6-mercapto-1-phenylcarbamoyl-hexyl)-amide,
(S)-6-oxo-piperidine-2-carboxylic acid [(S)-1-(3,4-dihydro-1H-isoquinoline-2-carbonyl)-6-mercapto-hexyl]-amide,
(R)-5-oxo-pyrrolidine-2-carboxylic acid ((S)-6-mercapto-1-phenylcarbamoyl-hexyl)-amide,
(S)-6-oxo-piperidine-2-carboxylic acid [(S)-6-mercapto-1-(2-m-tolyl-ethylcarbamoyl)-hexyl]-amide,
(R)-2-oxo-piperidine-3-carboxylic acid ((S)-6-mercapto-1-phenylcarbamoyl-hexyl)-amide,
(S)-2-oxo-piperidine-3-carboxylic acid ((S)-6-mercapto-1-phenylcarbamoyl-hexyl)-amide,
(R)-6-oxo-piperidine-2-carboxylic acid ((S)-6-mercapto-1-phenylcarbamoyl-hexyl)-amide,
thiocarbonic acid ethyl ester {(S)-6-[((S)-6-oxo-piperidine-2-carbonyl)-amino]-6-phenylcarbamoyl-hexyl}ester,
thioisobutyric acid S—{(S)-6-[((S)-6-oxo-piperidine-2-carbonyl)-amino]-6-phenylcarbamoyl-hexyl}ester,
thioacetic acid S—{(S)-6-[((S)-5-oxo-pyrrolidine-2-carbonyl)-amino]-6-phenylcarbamoyl-hexyl}ester,
thioacetic acid S—{(S)-6-[((S)-5-oxo-pyrrolidine-2-carbonyl)-amino]-6-m-tolylcarbamoyl-hexyl}ester,
thioacetic acid S—{(S)-6-[((R)-1-methyl-5-oxo-pyrrolidine-2-carbonyl)-amino]-6-phenylcarbamoyl-hexyl}ester,
thiocarbonic acid ethyl ester {(S)-6-[((R)-5-oxo-pyrrolidine-2-carbonyl)-amino]-6-phenylcarbamoyl-hexyl}ester,
thioacetic acid S—{(S)-6-[((R)-5-oxo-pyrrolidine-2-carbonyl)-amino]-6-m-tolylcarbamoyl-hexyl}ester,
thioacetic acid S—{(S)-6-[((R)-1-methyl-5-oxo-pyrrolidine-2-carbonyl)-amino]-6-m-tolylcarbamoyl-hexyl}ester,
thioacetic acid S—[(S)-6-[((R)-5-oxo-pyrrolidine-2-carbonyl)-amino]-6-(3-trifluoromethyl-phenylcarbamoyl)-hexyl]ester, thioacetic acid S—{(S)-6-[((S)-1-methyl-6-oxo-piperidine-2-carbonyl)-amino]-6-phenylcarbamoyl-hexyl}ester,
(S)-1-methyl-6-oxo-piperidine-2-carboxylic acid ((S)-6-mercapto-1-phenylcarbamoyl-hexyl)-amide,
(S)-6-oxo-piperidine-2-carboxylic acid ((S)-6-mercapto-1-m-tolylcarbamoyl-hexyl)-amide,
(S)-6-oxo-piperidine-2-carboxylic acid ((S)-6-mercapto-1-p-tolylcarbamoyl-hexyl)-amide, and
thioacetic acid S—{(S)-6-[((S)-6-oxo-1,2,3,6-tetrahydro-pyridine-2-carbonyl)-amino]-6-phenylcarbamoyl-hexyl}ester.

* * * * *